US009375316B2

(12) United States Patent
Meridew et al.

(10) Patent No.: US 9,375,316 B2
(45) Date of Patent: *Jun. 28, 2016

(54) METHOD AND APPARATUS FOR ACETABULAR RECONSTRUCTION

(71) Applicant: Biomet Manufacturing, LLC, Warsaw, IN (US)

(72) Inventors: Jason D. Meridew, Warsaw, IN (US); Phillip M. Gibbs, Winona Lake, IN (US)

(73) Assignee: BIOMET MANUFACTURING, LLC., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/046,244

(22) Filed: Oct. 4, 2013

(65) Prior Publication Data

US 2014/0039638 A1 Feb. 6, 2014

Related U.S. Application Data

(63) Continuation of application No. 13/405,683, filed on Feb. 27, 2012, now Pat. No. 8,551,181, and a continuation of application No. 11/768,510, filed on Jun. 26, 2007, now Pat. No. 8,123,814, and a (Continued)

(51) Int. Cl.
*A61F 2/32* (2006.01)
*A61F 2/34* (2006.01)
(Continued)

(52) U.S. Cl.
CPC ............... *A61F 2/34* (2013.01); *A61F 2/30724* (2013.01); *A61F 2/30734* (2013.01); *A61F 2/4684* (2013.01); *A61B 17/86* (2013.01); *A61F 2/30767* (2013.01); *A61F 2/4609* (2013.01); *A61F 2002/2835* (2013.01); *A61F 2002/3082* (2013.01); *A61F 2002/30153* (2013.01); *A61F 2002/30156* (2013.01);
(Continued)

(58) Field of Classification Search
USPC ............................................. 623/22.25, 22.28
See application file for complete search history.

(56) References Cited

U.S. PATENT DOCUMENTS 3,353,259 A 11/1967 Kirkpatrick
3,579,805 A 5/1971 Kast
(Continued)

FOREIGN PATENT DOCUMENTS

DE 2404214 8/1974
DE 3130732 5/1983
(Continued)

OTHER PUBLICATIONS

"Magnum™ large metal articulation, Surgical Technique" brochure, Biomet Orthopedics, Inc., 2004 (12 pages).
(Continued)

*Primary Examiner* — David H Willse
*Assistant Examiner* — Javier Blanco
(74) *Attorney, Agent, or Firm* — Schwegman Lundberg & Woessner, P.A.

(57) ABSTRACT

A trial system for a prosthesis is described. The prosthesis can include an acetabular prosthesis generally for implantation in an acetabulum and the surrounding pelvis. The acetabular prosthesis includes an acetabular cup having a substantially concave inner surface and a substantially convex outer surface. One trial shell or a collection of trial shells are provided to trial a range of motion of the hip joint before implanting a shell prosthesis into the acetabular prosthesis.

9 Claims, 19 Drawing Sheets

Related U.S. Application Data continuation-in-part of application No. 11/357,868, filed on Feb. 17, 2006, now Pat. No. 7,597,715, and a continuation-in-part of application No. 10/700,292, filed on Nov. 3, 2003, now Pat. No. 7,713,306, and a continuation-in-part of application No. 10/201,485, filed on Jul. 23, 2002, now Pat. No. 7,291,177, and a continuation-in-part of application No. 09/792,174, filed on Feb. 23, 2001, now Pat. No. 6,458,161.

(51) Int. Cl.
*A61F 2/30* (2006.01)
*A61B 17/86* (2006.01)
*A61F 2/46* (2006.01)
*A61F 2/28* (2006.01)

(52) U.S. Cl.
CPC ............. *A61F 2002/30327* (2013.01); *A61F 2002/30383* (2013.01); *A61F 2002/30433* (2013.01); *A61F 2002/30535* (2013.01); *A61F 2002/30553* (2013.01); *A61F 2002/30578* (2013.01); *A61F 2002/30616* (2013.01); *A61F 2002/30736* (2013.01); *A61F 2002/30774* (2013.01); *A61F 2002/30787* (2013.01); *A61F 2002/3291* (2013.01); *A61F 2002/3401* (2013.01); *A61F 2002/3404* (2013.01); *A61F 2002/4631* (2013.01); *A61F 2220/0025* (2013.01); *A61F 2220/0041* (2013.01); *A61F 2230/0019* (2013.01); *A61F 2230/0023* (2013.01); *A61F 2250/0008* (2013.01); *A61F 2250/0039* (2013.01); *A61F 2250/0058* (2013.01); *A61F 2250/0064* (2013.01); *A61F 2310/00017* (2013.01); *A61F 2310/00023* (2013.01); *A61F 2310/00029* (2013.01)

(56) References Cited

U.S. PATENT DOCUMENTS

| | | | |
|---|---|---|---|
| 3,605,123 A | 9/1971 | Hahn |
| 3,677,795 A | 7/1972 | Bokros et al. |
| 3,808,606 A | 5/1974 | Tronzo |
| 3,840,904 A | 10/1974 | Tronzo |
| 3,855,638 A | 12/1974 | Pilliar et al. |
| 3,896,500 A | 7/1975 | Rambert et al. |
| 3,905,777 A | 9/1975 | Lacroix et al. |
| 3,906,550 A | 9/1975 | Rostoker et al. |
| 3,938,499 A | 2/1976 | Bucalo |
| 3,986,212 A | 10/1976 | Sauer |
| 4,051,559 A | 10/1977 | Pifferi et al. |
| 4,156,943 A | 6/1979 | Collier |
| 4,164,794 A | 8/1979 | Spector et al. |
| 4,168,326 A | 9/1979 | Broemer et al. |
| 4,184,213 A | 1/1980 | Heimke et al. |
| 4,187,559 A | 2/1980 | Grell et al. |
| 4,205,400 A | 6/1980 | Shen et al. |
| 4,206,271 A | 6/1980 | Norling et al. |
| 4,217,666 A | 8/1980 | Averill |
| 4,224,698 A | 9/1980 | Hopson |
| 4,234,972 A | 11/1980 | Hench et al. |
| 4,285,070 A | 8/1981 | Averill |
| 4,307,472 A | 12/1981 | Morris |
| 4,309,488 A | 1/1982 | Heide et al. |
| 4,330,891 A | 5/1982 | Branemark et al. |
| 4,345,339 A | 8/1982 | Muller et al. |
| 4,351,069 A | 9/1982 | Ballintyn et al. |
| 4,355,428 A | 10/1982 | Deloison et al. |
| 4,362,681 A | 12/1982 | Spector et al. |
| 4,412,643 A | 11/1983 | Sato et al. |
| 4,479,271 A | 10/1984 | Bolesky et al. |
| 4,542,539 A | 9/1985 | Rowe, Jr. et al. |
| 4,550,448 A | 11/1985 | Kenna |
| 4,563,778 A | 1/1986 | Roche et al. |
| 4,566,138 A | 1/1986 | Lewis et al. |
| 4,570,271 A | 2/1986 | Sump |
| 4,612,160 A | 9/1986 | Donlevy et al. |
| 4,636,219 A | 1/1987 | Pratt et al. |
| 4,644,942 A | 2/1987 | Sump |
| 4,659,331 A | 4/1987 | Matthews et al. |
| 4,666,450 A | 5/1987 | Kenna |
| 4,685,923 A | 8/1987 | Mathys et al. |
| 4,693,721 A | 9/1987 | Ducheyne |
| 4,715,859 A | 12/1987 | Schelhas et al. |
| 4,715,860 A | 12/1987 | Amstutz et al. |
| 4,743,256 A | 5/1988 | Brantigan |
| 4,743,262 A | 5/1988 | Tronzo |
| 4,750,905 A | 6/1988 | Koeneman et al. |
| 4,756,862 A | 7/1988 | Spector et al. |
| 4,769,041 A | 9/1988 | Morscher et al. |
| 4,778,473 A | 10/1988 | Matthews et al. |
| 4,778,474 A | 10/1988 | Homsy |
| 4,795,469 A | 1/1989 | Oh |
| 4,801,301 A | 1/1989 | Noiles |
| 4,813,959 A | 3/1989 | Cremascoli et al. |
| 4,828,565 A | 5/1989 | Duthoit et al. |
| 4,840,632 A | 6/1989 | Kampner |
| 4,842,606 A | 6/1989 | Kranz et al. |
| 4,846,393 A | 7/1989 | Devillard |
| 4,851,006 A | 7/1989 | Tuke |
| 4,854,496 A | 8/1989 | Bugle |
| 4,863,474 A | 9/1989 | Brown et al. |
| 4,863,475 A | 9/1989 | Andersen et al. |
| 4,863,538 A | 9/1989 | Deckard |
| 4,871,368 A | 10/1989 | Wagner |
| 4,883,490 A | 11/1989 | Oh |
| 4,883,491 A | 11/1989 | Mallory et al. |
| 4,892,549 A | 1/1990 | Figgie, III et al. |
| 4,904,265 A | 2/1990 | MacCollum et al. |
| 4,919,666 A | 4/1990 | Buchhorn et al. |
| 4,919,675 A | 4/1990 | Dietschi et al. |
| 4,923,473 A | 5/1990 | Griss et al. |
| 4,936,847 A | 6/1990 | Manginelli |
| 4,936,856 A | 6/1990 | Keller |
| 4,936,861 A | 6/1990 | Muller et al. |
| 4,944,759 A | 7/1990 | Mallory et al. |
| 4,950,270 A | 8/1990 | Bowman et al. |
| 4,950,299 A | 8/1990 | Noiles |
| 4,955,919 A | 9/1990 | Pappas et al. |
| 4,957,819 A | 9/1990 | Kawahara et al. |
| 4,963,154 A | 10/1990 | Anapliotis et al. |
| 4,969,907 A | 11/1990 | Koch et al. |
| 4,969,910 A | 11/1990 | Frey et al. |
| 4,976,738 A | 12/1990 | Frey et al. |
| 4,978,355 A | 12/1990 | Frey et al. |
| 4,978,356 A | 12/1990 | Noiles |
| 4,978,358 A | 12/1990 | Bobyn |
| 4,997,445 A | 3/1991 | Hodorek |
| 5,002,577 A | 3/1991 | Bolesky et al. |
| 5,004,476 A | 4/1991 | Cook |
| 5,009,665 A | 4/1991 | Serbousek et al. |
| 5,013,324 A | 5/1991 | Zolman et al. |
| 5,018,285 A | 5/1991 | Zolman et al. |
| 5,019,105 A | 5/1991 | Wiley |
| 5,021,062 A | 6/1991 | Adrey et al. |
| 5,021,063 A | 6/1991 | Tager |
| 5,024,670 A | 6/1991 | Smith et al. |
| 5,027,998 A | 7/1991 | Bugle |
| 5,030,233 A | 7/1991 | Ducheyne |
| 5,047,182 A | 9/1991 | Sundback et al. |
| 5,080,672 A | 1/1992 | Bellis et al. |
| 5,080,674 A | 1/1992 | Jacobs et al. |
| 5,080,685 A | 1/1992 | Bolesky et al. |
| 5,084,051 A | 1/1992 | Tormala et al. |
| 5,092,897 A | 3/1992 | Forte |
| 5,096,518 A | 3/1992 | Fujikawa et al. |
| 5,098,435 A | 3/1992 | Stednitz et al. |
| 5,104,410 A | 4/1992 | Chowdhary |
| 5,108,432 A | 4/1992 | Gustavson |
| 5,120,175 A | 6/1992 | Arbegast et al. |
| 5,126,103 A | 6/1992 | Ishizaki et al. |
| 5,133,764 A | 7/1992 | Pappas et al. |

(56) References Cited

U.S. PATENT DOCUMENTS

| | | |
|---|---|---|
| 5,152,796 A | 10/1992 | Slamin |
| 5,152,797 A | 10/1992 | Luckman et al. |
| 5,156,626 A | 10/1992 | Broderick et al. |
| 5,163,961 A | 11/1992 | Harwin |
| 5,167,502 A | 12/1992 | Kawahara et al. |
| 5,176,711 A | 1/1993 | Grimes |
| 5,181,928 A | 1/1993 | Bolesky et al. |
| 5,192,329 A | 3/1993 | Christie et al. |
| 5,198,308 A | 3/1993 | Shetty et al. |
| 5,201,766 A | 4/1993 | Georgette |
| 5,203,787 A | 4/1993 | Noblitt et al. |
| 5,211,665 A | 5/1993 | Ku et al. |
| 5,226,915 A | 7/1993 | Bertin |
| 5,236,457 A | 8/1993 | Devanathan |
| 5,236,462 A | 8/1993 | Mikhail |
| 5,246,530 A | 9/1993 | Bugle et al. |
| 5,282,861 A | 2/1994 | Kaplan |
| 5,286,260 A | 2/1994 | Bolesky et al. |
| 5,290,315 A | 3/1994 | DeCarlo, Jr. |
| 5,310,408 A | 5/1994 | Schryver et al. |
| 5,314,490 A | 5/1994 | Wagner et al. |
| 5,323,954 A | 6/1994 | Shetty et al. |
| 5,326,367 A | 7/1994 | Robioneck et al. |
| 5,326,368 A | 7/1994 | Collazo |
| 5,343,877 A | 9/1994 | Park |
| 5,348,788 A | 9/1994 | White |
| 5,358,532 A | 10/1994 | Evans et al. |
| 5,360,448 A | 11/1994 | Thramann |
| 5,360,452 A | 11/1994 | Engelhardt et al. |
| 5,370,692 A | 12/1994 | Fink et al. |
| 5,370,698 A | 12/1994 | Heimke et al. |
| 5,370,702 A | 12/1994 | Jones |
| 5,370,704 A | 12/1994 | DeCarlo, Jr. |
| 5,370,706 A | 12/1994 | Bolesky et al. |
| 5,376,122 A | 12/1994 | Pappas et al. |
| 5,380,325 A | 1/1995 | Lahille et al. |
| 5,397,359 A | 3/1995 | Mittelmeier et al. |
| 5,405,389 A | 4/1995 | Conta et al. |
| 5,415,704 A | 5/1995 | Davidson |
| 5,443,510 A | 8/1995 | Shetty et al. |
| 5,443,512 A | 8/1995 | Parr et al. |
| 5,443,519 A | 8/1995 | Averill et al. |
| 5,484,539 A | 1/1996 | Tersi et al. |
| 5,486,181 A | 1/1996 | Cohen et al. |
| 5,496,372 A | 3/1996 | Hamamoto et al. |
| 5,504,300 A | 4/1996 | Devanathan et al. |
| 5,505,984 A | 4/1996 | England et al. |
| 5,507,824 A | 4/1996 | Lennox |
| 5,509,933 A | 4/1996 | Davidson et al. |
| 5,534,027 A | 7/1996 | Hodorek |
| 5,535,810 A | 7/1996 | Compton et al. |
| 5,540,713 A | 7/1996 | Schnepp-Pesch et al. |
| 5,545,227 A | 8/1996 | Davidson et al. |
| 5,549,685 A | 8/1996 | Hayes |
| 5,549,691 A | 8/1996 | Harwin |
| 5,549,698 A | 8/1996 | Averill et al. |
| 5,549,701 A | 8/1996 | Mikhail |
| 5,571,187 A | 11/1996 | Devanathan |
| 5,571,194 A | 11/1996 | Gabriel |
| 5,571,198 A | 11/1996 | Drucker et al. |
| 5,571,200 A | 11/1996 | Cohen et al. |
| 5,571,201 A | 11/1996 | Averill et al. |
| 5,573,401 A | 11/1996 | Davidson et al. |
| 5,591,233 A | 1/1997 | Kelman et al. |
| 5,593,451 A | 1/1997 | Averill et al. |
| 5,609,641 A | 3/1997 | Johnson et al. |
| 5,609,645 A | 3/1997 | Vinciguerra |
| 5,609,646 A | 3/1997 | Field et al. |
| 5,639,280 A | 6/1997 | Warner et al. |
| 5,658,338 A | 8/1997 | Tullos et al. |
| 5,658,347 A | 8/1997 | Sarkisian et al. |
| 5,658,348 A | 8/1997 | Rohr, Jr. |
| 5,665,119 A | 9/1997 | Koller |
| 5,676,700 A | 10/1997 | Black et al. |
| 5,676,704 A | 10/1997 | Ries et al. |
| 5,688,453 A | 11/1997 | England et al. |
| 5,702,458 A | 12/1997 | Burstein et al. |
| 5,702,473 A | 12/1997 | Albrektsson et al. |
| 5,702,477 A | 12/1997 | Capello et al. |
| 5,702,483 A | 12/1997 | Kwong |
| 5,702,487 A | 12/1997 | Averill et al. |
| 5,723,011 A | 3/1998 | Devanathan et al. |
| 5,723,014 A | 3/1998 | Laurent et al. |
| 5,725,587 A | 3/1998 | Garber |
| 5,728,510 A | 3/1998 | White |
| 5,734,959 A | 3/1998 | Krebs et al. |
| 5,755,743 A | 5/1998 | Volz et al. |
| 5,755,806 A | 5/1998 | Stalcup et al. |
| 5,782,928 A | 7/1998 | Ries et al. |
| 5,782,929 A | 7/1998 | Sederholm |
| 5,798,308 A | 8/1998 | Chatterjee et al. |
| 5,824,107 A | 10/1998 | Tschirren |
| 5,824,108 A | 10/1998 | Huebner |
| 5,863,295 A | 1/1999 | Averill et al. |
| 5,871,548 A | 2/1999 | Sanders et al. |
| 5,879,398 A | 3/1999 | Swarts et al. |
| 5,879,399 A | 3/1999 | Church |
| 5,879,401 A | 3/1999 | Besemer et al. |
| 5,879,404 A | 3/1999 | Bateman et al. |
| 5,879,405 A | 3/1999 | Ries et al. |
| 5,888,205 A | 3/1999 | Pratt et al. |
| 5,904,720 A | 5/1999 | Farrar et al. |
| 5,916,268 A | 6/1999 | Schollner et al. |
| 5,925,077 A | 7/1999 | Williamson et al. |
| 5,926,685 A | 7/1999 | Krebs et al. |
| 5,931,870 A | 8/1999 | Cuckler et al. |
| 5,938,702 A | 8/1999 | Lopez et al. |
| 5,972,032 A | 10/1999 | Lopez et al. |
| 5,976,148 A | 11/1999 | Charpenet et al. |
| 5,981,828 A | 11/1999 | Nelson et al. |
| 5,989,293 A | 11/1999 | Cook et al. |
| 6,008,432 A | 12/1999 | Taylor |
| 6,013,104 A | 1/2000 | Kampner |
| 6,022,509 A | 2/2000 | Matthews et al. |
| 6,042,611 A | 3/2000 | Noiles |
| 6,042,612 A | 3/2000 | Voydeville et al. |
| 6,049,054 A | 4/2000 | Panchison et al. |
| 6,059,833 A | 5/2000 | Doets |
| 6,063,442 A | 5/2000 | Cohen et al. |
| 6,066,176 A | 5/2000 | Oshida |
| 6,087,553 A | 7/2000 | Cohen et al. |
| 6,099,529 A | 8/2000 | Gertzman et al. |
| 6,129,765 A | 10/2000 | Lopez et al. |
| 6,132,469 A | 10/2000 | Schroeder |
| 6,132,674 A | 10/2000 | Compton et al. |
| 6,136,029 A | 10/2000 | Johnson et al. |
| 6,139,574 A | 10/2000 | Vacanti et al. |
| 6,143,036 A | 11/2000 | Comfort |
| 6,143,293 A | 11/2000 | Weiss et al. |
| 6,149,689 A | 11/2000 | Grundei et al. |
| 6,152,962 A | 11/2000 | DeCarlo, Jr. |
| 6,162,257 A | 12/2000 | Gustilo et al. |
| 6,165,222 A | 12/2000 | Hoeppner et al. |
| 6,176,879 B1 | 1/2001 | Reischl et al. |
| 6,187,050 B1 | 2/2001 | Khalili et al. |
| 6,192,272 B1 | 2/2001 | Fiedler et al. |
| 6,193,761 B1 | 2/2001 | Treacy |
| 6,197,065 B1 | 3/2001 | Martin et al. |
| 6,203,844 B1 | 3/2001 | Park |
| 6,206,924 B1 | 3/2001 | Timm |
| 6,217,620 B1 | 4/2001 | Park |
| 6,228,121 B1 | 5/2001 | Khalili |
| 6,231,612 B1 | 5/2001 | Balay et al. |
| 6,240,616 B1 | 6/2001 | Yan |
| 6,253,443 B1 | 7/2001 | Johnson |
| 6,273,891 B1 | 8/2001 | Masini |
| 6,290,726 B1 | 9/2001 | Pope et al. |
| 6,293,971 B1 | 9/2001 | Nelson et al. |
| 6,296,667 B1 | 10/2001 | Johnson et al. |
| 6,302,913 B1 | 10/2001 | Ripamonti et al. |
| 6,306,173 B1 | 10/2001 | Masini |
| 6,309,546 B1 | 10/2001 | Herrmann et al. |
| 6,312,201 B1 | 11/2001 | Nagaya et al. |
| 6,322,728 B1 | 11/2001 | Brodkin et al. |

(56) References Cited

U.S. PATENT DOCUMENTS

| | | |
|---|---|---|
| 6,340,370 B1 | 1/2002 | Willert et al. |
| 6,352,559 B1 | 3/2002 | Church |
| 6,365,092 B1 | 4/2002 | Backa et al. |
| 6,376,573 B1 | 4/2002 | White et al. |
| 6,391,251 B1 | 5/2002 | Keicher et al. |
| 6,416,553 B1 | 7/2002 | White et al. |
| 6,432,142 B1 | 8/2002 | Kamiya et al. |
| 6,443,991 B1 | 9/2002 | Running |
| 6,447,543 B1 | 9/2002 | Studer et al. |
| 6,447,550 B1 | 9/2002 | Hunter et al. |
| 6,454,811 B1 | 9/2002 | Sherwood et al. |
| 6,458,161 B1 | 10/2002 | Gibbs et al. |
| 6,461,385 B1 | 10/2002 | Gayer et al. |
| 6,475,243 B1 | 11/2002 | Sheldon et al. |
| 6,488,713 B1 | 12/2002 | Hershberger |
| 6,495,448 B1 | 12/2002 | Lee |
| 6,497,727 B1 | 12/2002 | Pope et al. |
| 6,506,192 B1 | 1/2003 | Gertzman et al. |
| 6,508,841 B2 | 1/2003 | Martin et al. |
| 6,520,995 B2 | 2/2003 | Church |
| 6,527,774 B2 | 3/2003 | Lieberman |
| 6,527,807 B1 | 3/2003 | O'Neil et al. |
| 6,527,809 B1 | 3/2003 | Doursounian et al. |
| 6,530,958 B1 | 3/2003 | Cima et al. |
| 6,537,321 B1 | 3/2003 | Horber |
| 6,544,472 B1 | 4/2003 | Compton et al. |
| 6,558,428 B2 | 5/2003 | Park |
| 6,572,655 B1 | 6/2003 | Johnson |
| 6,585,772 B2 | 7/2003 | Hunter et al. |
| 6,592,622 B1 | 7/2003 | Ferguson |
| 6,605,293 B1 | 8/2003 | Giordano et al. |
| 6,605,648 B1 | 8/2003 | Johnson et al. |
| 6,610,097 B2 | 8/2003 | Serbousek et al. |
| 6,613,093 B2 | 9/2003 | DeCarlo, Jr. et al. |
| 6,620,200 B1 | 9/2003 | Descamps et al. |
| 6,621,039 B2 | 9/2003 | Wang et al. |
| 6,626,947 B2 | 9/2003 | Lester et al. |
| 6,626,950 B2 | 9/2003 | Brown et al. |
| 6,641,616 B1 | 11/2003 | Grundei et al. |
| 6,645,206 B1 | 11/2003 | Zdeblick et al. |
| 6,652,586 B2 | 11/2003 | Hunter et al. |
| 6,660,040 B2 | 12/2003 | Chan et al. |
| 6,660,224 B2 | 12/2003 | Lefebvre et al. |
| RE38,409 E | 1/2004 | Noiles |
| 6,676,704 B1 | 1/2004 | Pope et al. |
| 6,676,892 B2 | 1/2004 | Das et al. |
| 6,682,566 B2 | 1/2004 | Draenert |
| 6,682,567 B1 | 1/2004 | Schroeder |
| 6,686,437 B2 | 2/2004 | Buchman et al. |
| 6,695,884 B1 | 2/2004 | Townley |
| 6,696,073 B2 | 2/2004 | Boyce et al. |
| 6,709,462 B2 | 3/2004 | Hanssen |
| 6,725,901 B1 | 4/2004 | Kramer et al. |
| 6,726,723 B2 | 4/2004 | Running |
| 6,726,725 B2 | 4/2004 | Hunter et al. |
| 6,740,186 B2 | 5/2004 | Hawkins et al. |
| 6,758,864 B2 | 7/2004 | Storer et al. |
| 6,770,099 B2 | 8/2004 | Andriacchi et al. |
| 6,783,551 B1 | 8/2004 | Metzger et al. |
| 6,800,094 B2 | 10/2004 | Burkinshaw |
| 6,811,569 B1 | 11/2004 | Afriat et al. |
| 6,827,742 B2 | 12/2004 | Hayes, Jr. et al. |
| 6,840,960 B2 | 1/2005 | Bubb |
| 6,866,685 B2 | 3/2005 | Chan et al. |
| 6,869,447 B2 | 3/2005 | Lee et al. |
| 6,896,703 B2 | 5/2005 | Barbieri et al. |
| 6,908,486 B2 | 6/2005 | Lewallen |
| 6,913,623 B1 | 7/2005 | Zhu |
| 6,916,342 B2 | 7/2005 | Frederick et al. |
| 6,923,833 B2 | 8/2005 | Wasielewski |
| 6,926,740 B2 | 8/2005 | Lewis et al. |
| 6,945,448 B2 | 9/2005 | Medlin et al. |
| 6,976,999 B2 | 12/2005 | Charlebois et al. |
| 6,981,991 B2 | 1/2006 | Ferree |
| 7,141,073 B2 | 11/2006 | May et al. |
| 7,147,819 B2 | 12/2006 | Bram et al. |
| 7,156,880 B2 | 1/2007 | Evans et al. |
| 7,166,133 B2 | 1/2007 | Evans et al. |
| 7,189,263 B2 | 3/2007 | Erbe et al. |
| 7,192,448 B2 | 3/2007 | Ferree |
| 7,291,177 B2 | 11/2007 | Gibbs |
| 7,351,371 B2 | 4/2008 | Nelles et al. |
| 7,597,715 B2 | 10/2009 | Brown et al. |
| 7,635,447 B2 | 12/2009 | Hamman et al. |
| 7,713,306 B2 | 5/2010 | Gibbs |
| 7,883,661 B2 | 2/2011 | Hamman et al. |
| 8,021,432 B2 | 9/2011 | Meridew et al. |
| 8,066,778 B2 | 11/2011 | Meridew et al. |
| 8,123,814 B2 | 2/2012 | Meridew et al. |
| 8,197,550 B2 | 6/2012 | Brown et al. |
| 8,266,780 B2 | 9/2012 | Bollinger et al. |
| 8,292,967 B2 | 10/2012 | Brown et al. |
| 8,361,380 B2 | 1/2013 | Hamman et al. |
| 8,383,033 B2 | 2/2013 | Gupta |
| 8,551,181 B2 | 10/2013 | Meridew et al. |
| 8,814,978 B2 | 8/2014 | Hamman et al. |
| 8,951,465 B2 | 2/2015 | Gupta |
| 2001/0011190 A1 | 8/2001 | Park |
| 2001/0013166 A1 | 8/2001 | Yan |
| 2001/0030035 A1 | 10/2001 | Oda |
| 2002/0016635 A1 | 2/2002 | Despres et al. |
| 2002/0040245 A1 | 4/2002 | Lester et al. |
| 2002/0062154 A1 | 5/2002 | Ayers |
| 2002/0068980 A1 | 6/2002 | Serbousek et al. |
| 2002/0071827 A1 | 6/2002 | Petersen et al. |
| 2002/0123750 A1 | 9/2002 | Eisermann et al. |
| 2002/0139504 A1 | 10/2002 | Klein |
| 2002/0143403 A1 | 10/2002 | Vaidyanathan et al. |
| 2002/0151983 A1 | 10/2002 | Shetty |
| 2002/0197178 A1 | 12/2002 | Yan |
| 2003/0001282 A1 | 1/2003 | Meynen et al. |
| 2003/0013989 A1 | 1/2003 | Obermiller et al. |
| 2003/0033020 A1 | 2/2003 | Hunter et al. |
| 2003/0049299 A1 | 3/2003 | Malaviya et al. |
| 2003/0050703 A1 | 3/2003 | Harris et al. |
| 2003/0050705 A1 | 3/2003 | Cueille et al. |
| 2003/0069639 A1 | 4/2003 | Sander et al. |
| 2003/0074079 A1 | 4/2003 | McTighe et al. |
| 2003/0083741 A1 | 5/2003 | Woo et al. |
| 2003/0105529 A1 | 6/2003 | Synder et al. |
| 2003/0111752 A1 | 6/2003 | Wood et al. |
| 2003/0114936 A1 | 6/2003 | Sherwood et al. |
| 2003/0135281 A1 | 7/2003 | Hanssen |
| 2003/0144741 A1 | 7/2003 | King et al. |
| 2003/0144742 A1 | 7/2003 | King et al. |
| 2003/0153203 A1 | 8/2003 | Ketelsleger |
| 2003/0153981 A1 | 8/2003 | Wang et al. |
| 2003/0153982 A1 | 8/2003 | Pria |
| 2003/0155686 A1 | 8/2003 | Hawkins et al. |
| 2003/0163202 A1 | 8/2003 | Lakin |
| 2003/0163203 A1 | 8/2003 | Nycz et al. |
| 2003/0171818 A1 | 9/2003 | Lewallen |
| 2003/0171820 A1 | 9/2003 | Wilshaw et al. |
| 2003/0200837 A1 | 10/2003 | Matsuura et al. |
| 2003/0220696 A1 | 11/2003 | Levine et al. |
| 2003/0232124 A1 | 12/2003 | Medlin et al. |
| 2003/0236573 A1 | 12/2003 | Evans et al. |
| 2004/0054418 A1 | 3/2004 | McLean et al. |
| 2004/0054421 A1 | 3/2004 | McLean |
| 2004/0064192 A1 | 4/2004 | Bubb |
| 2004/0072010 A1 | 4/2004 | Date et al. |
| 2004/0083004 A1 | 4/2004 | Wasielewski |
| 2004/0088038 A1 | 5/2004 | Dehnad et al. |
| 2004/0098127 A1 | 5/2004 | Charlebois et al. |
| 2004/0102854 A1 | 5/2004 | Zhu |
| 2004/0109853 A1 | 6/2004 | McDaniel |
| 2004/0122521 A1 | 6/2004 | Lee et al. |
| 2004/0126265 A1 | 7/2004 | Takiguchi |
| 2004/0126583 A1 | 7/2004 | Nakamura et al. |
| 2004/0137218 A1 | 7/2004 | Liu et al. |
| 2004/0166340 A1 | 8/2004 | Cairns et al. |
| 2004/0172137 A1 | 9/2004 | Blaylock et al. |
| 2004/0186553 A1 | 9/2004 | Yan |
| 2004/0199258 A1 | 10/2004 | Macara |

(56) References Cited

U.S. PATENT DOCUMENTS

| | | |
|---|---|---|
| 2004/0199260 A1 | 10/2004 | Pope et al. |
| 2004/0210316 A1 | 10/2004 | King et al. |
| 2004/0225369 A1 | 11/2004 | Lakin et al. |
| 2004/0225371 A1 | 11/2004 | Roger |
| 2004/0229029 A1 | 11/2004 | Bowles et al. |
| 2004/0238410 A1 | 12/2004 | Inoue et al. |
| 2004/0243133 A1 | 12/2004 | Materna |
| 2005/0004677 A1 | 1/2005 | Johnson |
| 2005/0004678 A1 | 1/2005 | Richards |
| 2005/0004680 A1 | 1/2005 | Saladino et al. |
| 2005/0010303 A1 | 1/2005 | Nogier |
| 2005/0025656 A1 | 2/2005 | Bhaduri et al. |
| 2005/0031704 A1 | 2/2005 | Ahn |
| 2005/0032025 A1 | 2/2005 | Bhaduri et al. |
| 2005/0033298 A1 | 2/2005 | Hawkes et al. |
| 2005/0035052 A1 | 2/2005 | Kelly et al. |
| 2005/0048193 A1 | 3/2005 | Li et al. |
| 2005/0049713 A1 | 3/2005 | Garber et al. |
| 2005/0060040 A1 | 3/2005 | Auxepaules et al. |
| 2005/0065307 A1 | 3/2005 | King et al. |
| 2005/0065604 A1 | 3/2005 | Stoll |
| 2005/0071015 A1 | 3/2005 | Sekel |
| 2005/0085820 A1 | 4/2005 | Collins et al. |
| 2005/0085915 A1 | 4/2005 | Steinberg |
| 2005/0087915 A1 | 4/2005 | Pope et al. |
| 2005/0090905 A1 | 4/2005 | Hawkins et al. |
| 2005/0100470 A1 | 5/2005 | Lefebvre et al. |
| 2005/0107883 A1 | 5/2005 | Goodfried et al. |
| 2005/0145364 A1 | 7/2005 | Goodfried et al. |
| 2005/0149199 A1 | 7/2005 | Steinberg |
| 2005/0171614 A1 | 8/2005 | Bacon |
| 2005/0184134 A1 | 8/2005 | Charlebois et al. |
| 2005/0234559 A1 | 10/2005 | Fernandez et al. |
| 2005/0242162 A1 | 11/2005 | Medlin et al. |
| 2005/0246032 A1 | 11/2005 | Bokros et al. |
| 2006/0002810 A1 | 1/2006 | Grohowski |
| 2006/0003179 A1 | 1/2006 | Wang et al. |
| 2006/0018942 A1 | 1/2006 | Rowe et al. |
| 2006/0200247 A1 | 9/2006 | Charrois |
| 2006/0241776 A1 | 10/2006 | Brown et al. |
| 2006/0241781 A1 | 10/2006 | Brown et al. |
| 2007/0021838 A1 | 1/2007 | Dugas et al. |
| 2007/0129809 A1 | 6/2007 | Meridew et al. |
| 2007/0150068 A1 | 6/2007 | Dong et al. |
| 2007/0173948 A1 | 7/2007 | Meridew et al. |
| 2007/0196230 A1 | 8/2007 | Hamman et al. |
| 2007/0219640 A1 | 9/2007 | Steinberg |
| 2007/0243312 A1 | 10/2007 | Bulko |
| 2007/0250175 A1 | 10/2007 | Meridew et al. |
| 2007/0264152 A1 | 11/2007 | Zhao |
| 2008/0027548 A1 | 1/2008 | Metzger |
| 2008/0147187 A1 | 6/2008 | Bollinger et al. |
| 2008/0195222 A1 | 8/2008 | Rauguth et al. |
| 2008/0199343 A1 | 8/2008 | Rust et al. |
| 2009/0084491 A1 | 4/2009 | Uthgenannt et al. |
| 2009/0098310 A1 | 4/2009 | Hippensteel et al. |
| 2010/0003155 A1 | 1/2010 | Hamman et al. |
| 2010/0004754 A1 | 1/2010 | Brown et al. |
| 2010/0074789 A1 | 3/2010 | Heuer et al. |
| 2012/0150311 A1 | 6/2012 | Meridew et al. |
| 2013/0118377 A1 | 5/2013 | Hamman et al. |
| 2013/0177467 A1 | 7/2013 | Gupta |

FOREIGN PATENT DOCUMENTS

| | | |
|---|---|---|
| DE | 3205526 | 9/1983 |
| DE | 8612735 | 3/1989 |
| DE | 4133433 | 5/1993 |
| DE | 19726961 | 11/1998 |
| EP | 0214885 | 3/1987 |
| EP | 0378928 | 7/1990 |
| EP | 0538987 A1 | 4/1993 |
| EP | 0551794 | 7/1993 |
| EP | 0612509 | 8/1994 |
| EP | 0648478 | 4/1995 |
| EP | 0806921 | 11/1997 |
| EP | 0807426 | 11/1997 |
| EP | 0807426 A2 | 11/1997 |
| EP | 0985386 A2 | 3/2000 |
| EP | 1082949 | 3/2001 |
| EP | 1082949 A1 | 3/2001 |
| EP | 1236450 | 9/2002 |
| EP | 1312323 A2 | 5/2003 |
| EP | 1384456 | 1/2004 |
| EP | 1421918 A1 | 5/2004 |
| EP | 1430856 A1 | 6/2004 |
| FR | 2148322 | 3/1973 |
| FR | 2775586 | 9/1999 |
| GB | 2001247 | 1/1979 |
| JP | 2003325654 | 11/2003 |
| JP | 2006-043199 A | 2/2006 |
| JP | 3837502 B2 | 10/2006 |
| WO | WO-9218069 | 10/1992 |
| WO | WO-9613233 A1 | 5/1996 |
| WO | WO-9623459 | 8/1996 |
| WO | WO-0038598 A1 | 7/2000 |
| WO | WO-0170141 | 9/2001 |
| WO | WO-0207652 | 1/2002 |
| WO | WO-2004069107 | 8/2004 |
| WO | WO-2004080340 | 9/2004 |
| WO | WO-2006007861 | 1/2006 |
| WO | WO-2007097949 A2 | 8/2007 |
| WO | WO-2008103457 A2 | 8/2008 |
| WO | WO-2009042150 A1 | 4/2009 |
| WO | WO-2009108788 A1 | 9/2009 |
| WO | WO-2009108788 A1 | 9/2009 |
| WO | WO-2011044330 A1 | 4/2011 |

OTHER PUBLICATIONS

Bram, Martin, et al., High-Porosity Titanium, Stainless Steel, and Superalloy Parts, Advanced Engineering Materials 2000, 2, No. 4, 196-199.
European Search Report for EP03254588.1 mailed Aug. 22, 2006.
European Search Report for EP04256566.3 mailed Aug. 25, 2006.
European Search Report for EP07750635.0 mailed Jan. 27, 2012.
European Search Report mailed Jul. 12, 2007 for European Application No. 07250588.6.
International Preliminary Report on Patentability for PCT/US2007/003811 mailed Aug. 28, 2008.
International Preliminary Report on Patentability for PCT/US2008/002372 mailed Sep. 3, 2009.
International Preliminary Report on Patentability for PCT/US2009/035303 mailed Sep. 10, 2010.
International Preliminary Report on Patentability for PCT/US2010/051775 mailed Apr. 19, 2012.
International Search Report and Written Opinion for PCT/US2007/03811 mailed Sep. 27, 2007.
International Search Report and Written Opinion for PCT/US2008/002372 mailed Dec. 9, 2008 claiming benefit of U.S. Appl. No. 11/709,549, which claims benefit of U.S. Appl. No. 11/546,500, which claims benefit of U.S. Appl. No. 11/357,868, whichclaims benefit of U.S. Appl. No. 11/294,692, which claims benefit of U.S. Appl. No. 11/111,123.
International Search Report and Written Opinion for PCT/US2008/002372 mailed Jul. 30, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.
International Search Report and Written Opinion mailed Jul. 28, 2009 for PCT/US2009/035303 claiming benefit of U.S. Appl. No. 12/038,570, filed Feb. 27, 2008; which is a continuation-in-part of U.S. Appl. No. 11/294,692, filed Dec. 5, 2005; which is a continuation-in-part of U.S. Appl. No. 11/111,123, filed Apr. 21, 2005.
International Search Report for PCT/US2010/051775 mailed Mar. 24, 2011.
Invitation to Pay Additional Fees for PCT/US2008/002372 mailed Jul. 30, 2008 claiming benefit of U.S. Appl. No. 11/709,549, which

(56) References Cited

OTHER PUBLICATIONS claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

Laptev, A. et al. "Study of Production Route for Titanium Parts Combining Very High Porosity and Complex Shape" Powder Metallurgy, vol. 47, No. 1 (2004), pp. 85-92.

Li, J. et al. "A Novel Porous Ti6Al4V: Characterization and Cell Attachment" Journal of Biomedical Materials Research, vol. 73a, No. 2, pp. 223-233 (May 2005).

Magnum™ large metal articulation, Surgical Technique, brochure, Biomet Orthopedics, Inc., 12 pages (2004).

Mahoney, M. and Bampton, C. "Fundamentals of Diffusion Bonding" ASM Handbook, vol. 6 (1994), pp. 156-159.

Michael S. Bradford, M.D. and Wayne G. Paprosky, M.D., F.A.C.S., Total Acetabular Transplant Allograft Reconstruction of the Severely Deficient Acetabulum, Sunrise Hospital and Medical Center, Las Vegas, NV and Rush-Presbyterian-St. Lukes MedicalCenter, Chicago, IL, 1995 by W.B. Saunders Company, pp. 1-15.

Office Action issued in Related CN Application No. 2008800087328 dated Jun. 29, 2011.

Office Action issued in Related JP Application No. 2008555311 dated Aug. 23, 2011.

Oliveira, M. V., et al., Porous Structure Characterization in Titanium Coating for Surgical Implants, .COPYRGT. 2002, Materials Research, vol. 5, No. 3, 269-273.

Overview of Anatomy, Clinically Oriented Anatomy, pp. 1-16.

Wen, C. E., et al., Novel titanium foam for bone tissue engineering, J. Mater. Res., vol. 17, No. 10, Oct. 2002, 2633-2639.

Wen, C. E., et al., Processing and mechanical properties of autogenous titanium implant materials, Journal of Materials Science: Materials in Medicine 13 (2002), 397-401.

Wen, C. E., Processing of biocompatible porous Ti and Mg, Scripta Materialia 45 (2001) 1147-1153.

Wheeler, K. R., et al., Porous Metals as a Hard Tissue Substitute. Part II. Porous Metal Properties, Biomat., Med. Dev., Art. Org., 1(2), 337-348 (1973).

European Communication Pursuant to Article 94(3) EPC mailed Feb. 13, 2015 for European Patent Application No. 03254588.1.

European Communication Pursuant to Article 94(3) EPC mailed Mar. 3, 2011 for European Patent Application No. 03254588.1.

"U.S. Appl. No. 11/768,510, Applicant's Summary of Examiner Interview filed Nov. 14, 2011", 2 pgs.

"U.S. Appl. No. 11/768,510, Non Final Office Action mailed Apr. 27, 2011", 15 pgs.

"U.S. Appl. No. 11/768,510, Notice of Allowance mailed Oct. 21, 2011", 14 pgs.

"U.S. Appl. No. 11/768,510, Preliminary Amendment filed Apr. 19, 2011", 14 pgs.

"U.S. Appl. No. 11/768,510, Response filed Feb. 22, 2011 to Restriction Requirement mailed Jan. 19, 2011", 4 pgs.

"U.S. Appl. No. 11/768,510, Response filed Aug. 4, 2011 to Non Final Office Action mailed Apr. 27, 2011", 27 pgs.

"U.S. Appl. No. 11/768,510, Restriction Requirement mailed Jan. 19, 2011", 7 pgs.

"U.S. Appl. No. 13/405,683, Applicant's Summary of Examiner Interview filed Jun. 3, 2013", 9 pgs.

"U.S. Appl. No. 13/405,683, Notice of Allowance mailed Jun. 6, 2013", 17 pgs.

"U.S. Appl. No. 13/405,683, Response filed Apr. 5, 2013 to Restriction Requirement mailed Mar. 5, 2013", 4 pgs.

"U.S. Appl. No. 13/405,683, Restriction Requirement mailed Mar. 5, 2013", 6 pgs.

"European Application Serial No. 08725961.0, Examination Notification Art. 94(3) mailed Feb. 10, 2015", 4 pgs.

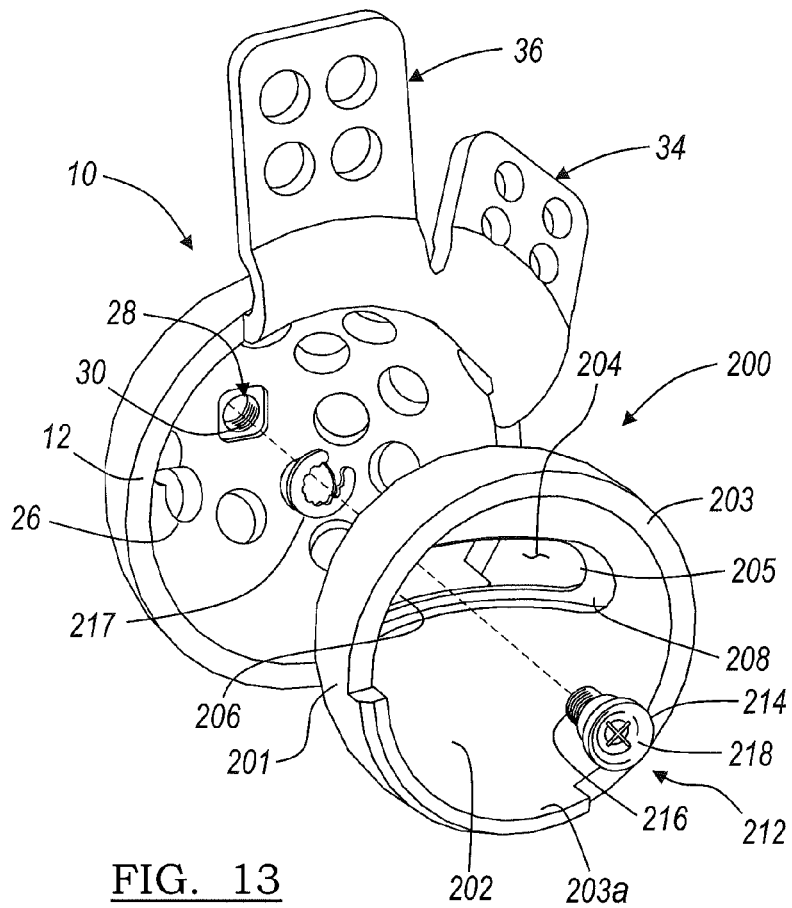
FIG. 13
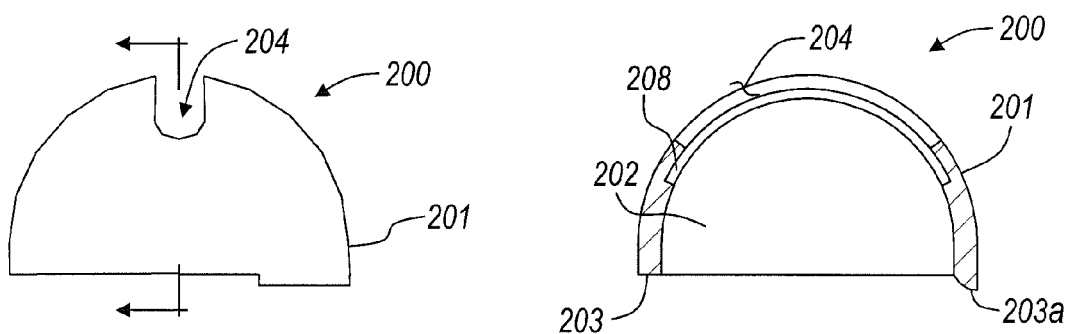
FIG. 14
FIG. 15

METHOD AND APPARATUS FOR ACETABULAR RECONSTRUCTION

CROSS-REFERENCE TO RELATED APPLICATIONS

This application is a continuation of U.S. Ser. No. 13/405,683 filed Feb. 27, 2012, now U.S. Pat. No. 8,551,181 issued Oct. 8, 2013; which is a continuation of U.S. Ser. No. 11/768,510 filed Jun. 26, 2007, now U.S. Pat. No. 8,123,814 issued Feb. 28, 2012; which is a continuation-in-part of: (1.) U.S. Ser. No. 11/357,868 filed Feb. 17, 2006, now U.S. Pat. No. 7,597,715 issued Oct. 6, 2009; and (2.) U.S. Ser. No. 10/700,292 filed Nov. 3, 2003, now U.S. Pat. No. 7,713,306 issued May 11, 2010; which is a continuation-in-part of U.S. Ser. No. 10/201,485 filed Jul. 23, 2002, now U.S. Pat. No. 7,291,177 issued Nov. 6, 2007; which is a continuation-in-part of U.S. Ser. No. 09/792,174 filed Feb. 23, 2001, now U.S. Pat. No. 6,458,161, issued Oct. 1, 2002. The disclosures of the above applications are incorporated herein by reference.

FIELD

This invention relates generally to a method and apparatus for use in orthopedic surgery and, more particularly, to a method and apparatus for trialing a modular acetabular prosthesis having various modular attachment components for use during an orthopedic surgical procedure.

BACKGROUND

A natural hip joint may undergo degenerative changes due to a variety of etiologies. When these degenerative changes become so far advanced and irreversible, it may ultimately become necessary to replace a natural hip joint with a prosthetic hip. When implantation of such a hip joint prosthesis becomes necessary, the head of the femur, the acetabular, or both may need to be replaced. The head of the natural femur is first resected and a cavity is created within the intramedullary canal of the host femur for accepting the hip prosthesis. The hip prosthesis may be inserted and supported within the host femur by cementing the hip prosthesis within the host femur. Alternatively, the hip prosthesis may be impacted into the host femur so that it is snugly fit and supported by the host femur. If the acetabulum also needs repair, all remnants of articular cartilage are generally removed from the acetabulum and an acetabular prosthesis which will accommodate the head or ball of the hip prosthesis is affixed to the acetabulum. The acetabular prosthesis is affixed to the acetabulum by means of cement, screws or other appropriate fixation means.

Due to any number of reasons, however, a small portion of patients that undergo such orthopedic surgical procedures may require subsequent revision surgery to replace the prosthetic device with a new prosthetic device generally referred to as a revision prosthesis. One example of such a device is generally known as a protrusio cage.

In this regard, a revision acetabular prosthesis will generally include additional mounting points, such as integral extension members or hooks that provide additional stability for the revision acetabular prosthesis. These additional mounting points are generally required due to additional bone loss or defects exhibited at the acetabulum, such as collar/rim defects or pelvic discontinuity defects.

Various types of revision acetabular prostheses are currently available and different surgeons prefer different types of revision acetabular prostheses. Some surgeons prefer to use what is known as an ilium flange that is formed integral with the acetabular prosthesis and enables further securement of the acetabular prosthesis in the ilium region of the pelvis. Other surgeons prefer to use what is known as an obturator hook that is able to provide inferior fixation of the acetabular prosthesis by engaging the obturator foramen which is a large aperture adjacent the acetabulum. Because of this, a hospital must maintain a large inventory of different revision acetabular cups to meet the various surgeons' preferences. Moreover, the surgeon generally requires several revision acetabular cups available during surgery to account for any type of condition that may arise during the surgical procedure. This increased inventory of prosthetic devices increases the overall hospital costs and inventory control. Furthermore, by requiring the multiple revision acetabular cups to be available during the surgical procedure, multiple prosthetic devices must be sterilized prior to the surgical procedure, thereby increasing the surgical time, cost and complexity.

Regardless of the reason for the revision implant, or the use of the protrusio cage acetabular implant, the use of such a system requires first affixing the cage to the bone portion remaining in the patient and then affixing an acetabular shell or liner relative to the cage. The cage assists in reinforcing the bone structure of the patient, while the shell provides the bearing surface for the head of the femur or the ball of the implant.

The shell may be made out of any appropriate material, but is generally made of an ultra high molecular weight polyethylene. The shell is generally affixed into the protrusio cage with bone cement to complete the acetabular reconstruction. Because of this two piece system and type of attachment, however, it is often difficult for the surgeon to precisely implant the shell due to the relatively unconstrained possibilities of placing the shell in the protrusio cage. Moreover, there is not a way of fixing the shell within the protrusio cage before implanting the shell into the cage to test a range of motion of the hip joint after implantation into the shell.

In addition to, or alternative to a protrusio cage, an acetabular prosthesis can be used with a trialing system. For example, an acetabular cup implant can be fixed to a prepared acetabulum and a bearing liner can be positioned relative to the cup. The cup may be formed of a porous material that allows the bearing liner to be cemented to the interior of the cup. Nevertheless, it may be desirable to trial positions of the bearing liner relative to the cup prior to cementing the bearing liner relative to the cup.

Therefore, it is desired to provide a protrusio cage and shell implant that will allow a trialing of the hip joint through a range of motion before affixing the shell to the protrusio cage. Moreover, it is desired to provide a protrusio cage, which will allow for a trialing shell to be selectively and removably affixed to the implanted protrusio cage so that a hip joint may be trialed through a range of motion before affixing the implant shell. Finally, it is also desired to provide a collection of trial shells each having one degree of freedom and mountable in a distal orientation with respect to the protrusio cage, that may be placed in the resected acetabulum to determine a proper orientation of the protrusio cage before implanting the final cage.

SUMMARY OF THE DISCLOSURE

A system to provide a determination of an alignment of a prosthetic bearing in an acetabular prosthesis includes a trial shell having an attachment device thereon. An attachment member is moveable between a locating position and a fastened position to selectively and operably interconnect the trial shell to the acetabular prosthesis at the attachment device. The trial shell is moveable in one degree of freedom around an axis defined by the attachment member in the locating position and substantially immobile relative to the acetabular prosthesis in the fastened position.

In other features an acetabular cup generally defines a portion of a hollow sphere and includes a bore therein. The attachment member engages the bore in the locating position and the fastened position. The attachment member includes an attachment end engaged with the bore and a central portion extending between the attachment device. An engagement end manipulates the attachment member between the locating and the fastened position.

The acetabular cup includes an outer rim defining an acetabular cup plane. The trial shell includes an outer rim defining a trial shell plane. The location of the attachment device determines a predetermined angle the trial plane is oriented from the acetabular cup plane.

A method of implanting an acetabular prosthesis in an acetabulum and providing a liner in the acetabular prosthesis in a selected orientation includes implanting the acetabular prosthesis. A first trial shell is disposed in the acetabular prosthesis, the first shell having an outer dimension defining a first plane and extending at a first angle from the acetabular prosthesis. The first trial shell, having one degree of freedom, is oriented in a first orientation. The first trial shell is fixed in the first orientation. A femur is moved through a range of motion relative to the first trial shell.

According to other features, the first trial shell is removed. A second trial shell is disposed in the acetabular prosthesis. The second trial shell has an outer dimension defining a second plane and extends at a second angle from the acetabular prosthesis. The second angle is distinct from the first angle. The second trial shell, having one degree of freedom, is oriented in a second orientation. The second trial shell is fixed in the second orientation. The femur is moved through a range of motion relative to the second trial shell.

According to various embodiments, a system to provide an acetabular prosthesis to the anatomy is disclosed. The system can include a prosthetic cup to be positioned in a prepared acetabulum of the anatomy. A trial liner can be positioned in a first position relative to the prosthetic cup and a trial cement mantle can be placed between the prosthetic cup and the trial liner to assist in holding the trial liner relative to the prosthetic cup in the first position. A liner implant can also be provided for implantation.

According to various embodiments, a system to provide an acetabular prosthesis to the anatomy is disclosed. The system can include an implantable cup having a convex exterior surface and a concave interior surface, wherein each of the exterior surface and the interior surface includes a substantially porous material. A liner can be cemented to the interior of the implantable cup. A trial liner can be positioned in a first position relative to the implantable cup and a trial cement mantle, including an engagement portion to cooperate with the implantable cup, can be provided to substantially immovably hold the trial cement mantle relative to the implantable cup.

According to various embodiments, a method of providing an acetabular prosthesis to the anatomy is disclosed. The method can include positioning a cup relative to the anatomy and positioning a trial cement mantle member in a selected first position relative to the positioned cup. A trial liner can be positioned relative to the trial cement mantle member and the trial liner can be held in a first position relative to the trial cement mantle while moving a second portion relative to the held trial liner.

A more complete appreciation of the present invention and its scope can be obtained from the following detailed description of the invention, the drawings and the appended claims.

BRIEF DESCRIPTION OF THE DRAWINGS

The present invention will become more fully understood from the detailed description and the accompanying drawings, wherein:

FIG. 13 is an exploded perspective view of a trialing cup and a protrusio cage;

FIG. 14 is an elevational view of a trialing cup;

FIG. 15 is a cross-sectional view of a trialing cup;

FIG. 17B is a protrusio cage implanted in an acetabulum and the trialing cup in a second position different from that illustrated in FIG. 17a;

The same reference numerals refer to the same parts throughout the various Figures.

DETAILED DESCRIPTION OF THE EMBODIMENTS

Figure 1:
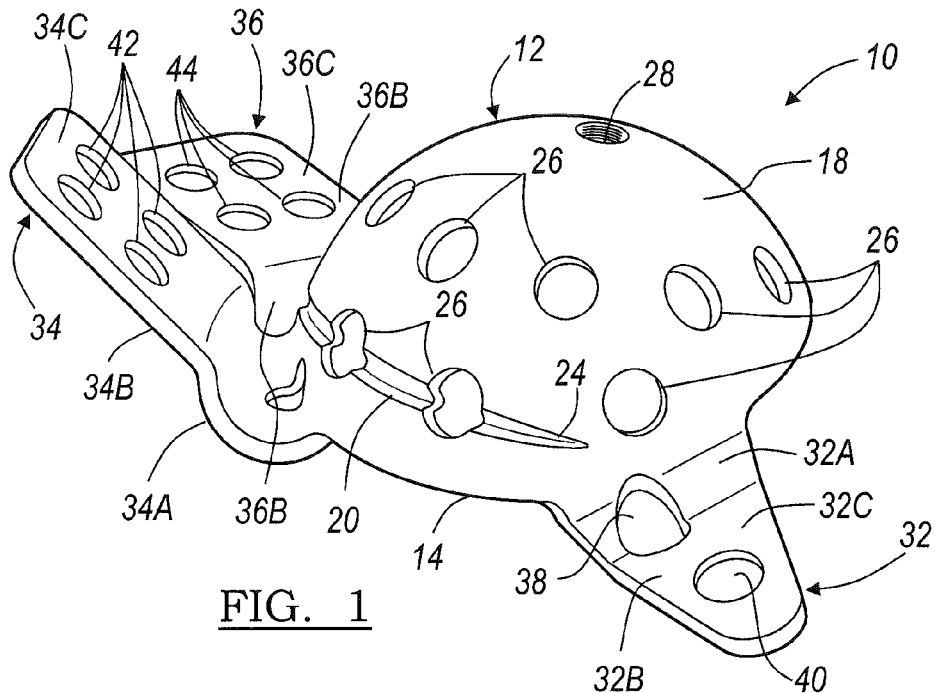
FIG. 1 is a rear perspective view of an acetabular prosthesis, in accordance with one embodiment of the present invention.
Figure 2:
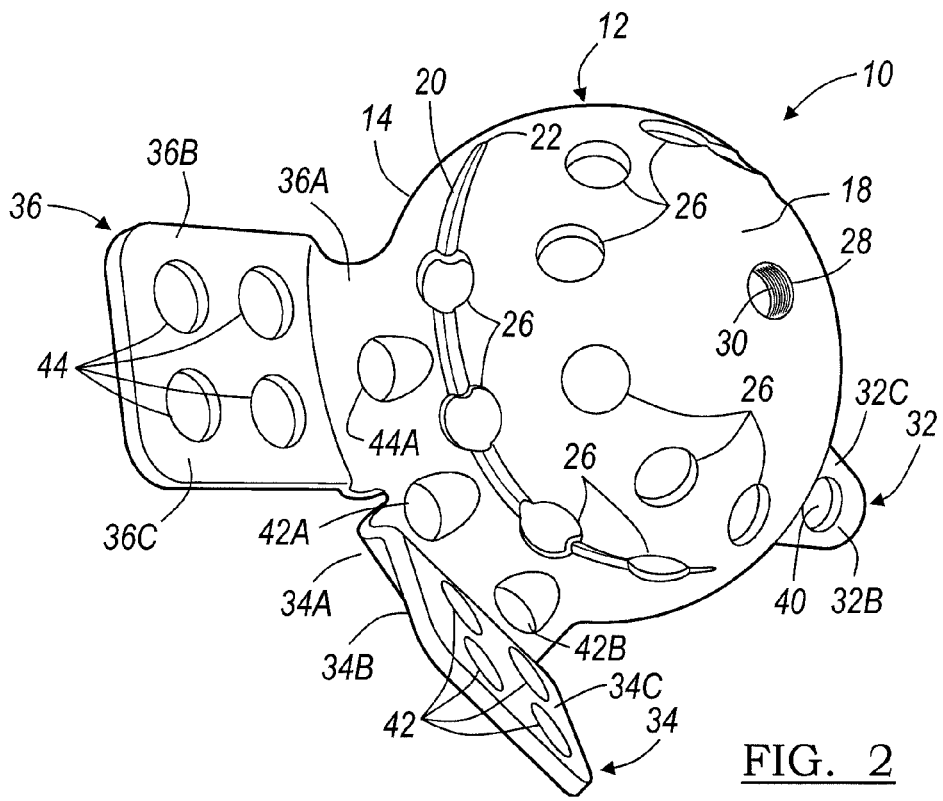
FIG. 2 is another rear perspective view of an acetabular prosthesis, in accordance with one embodiment of the present invention.
Figure 3:
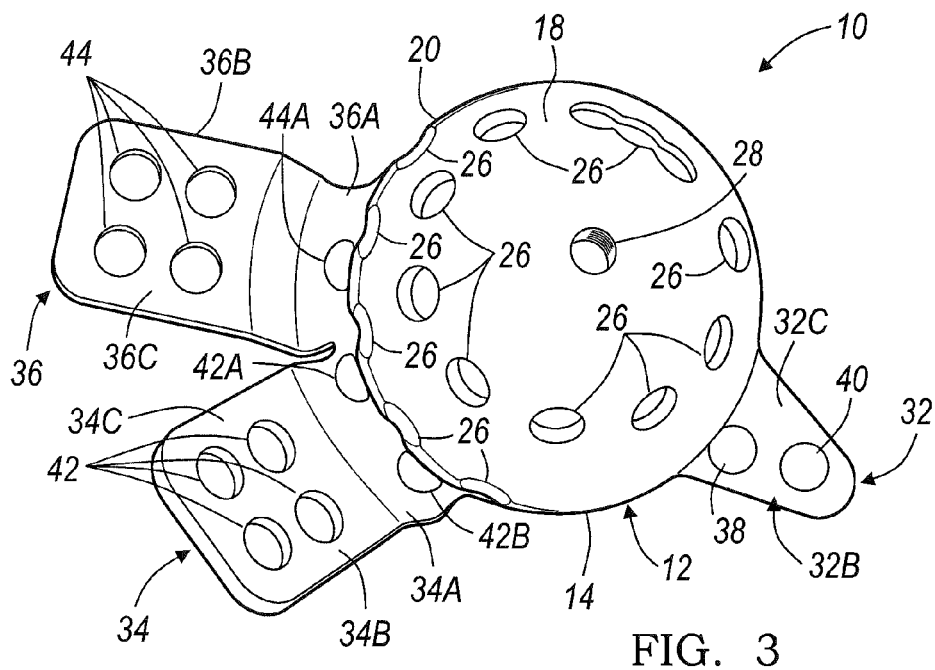
FIG. 3 is a rear elevational view of an acetabular prosthesis, in accordance with one embodiment of the present invention.
Figure 4:
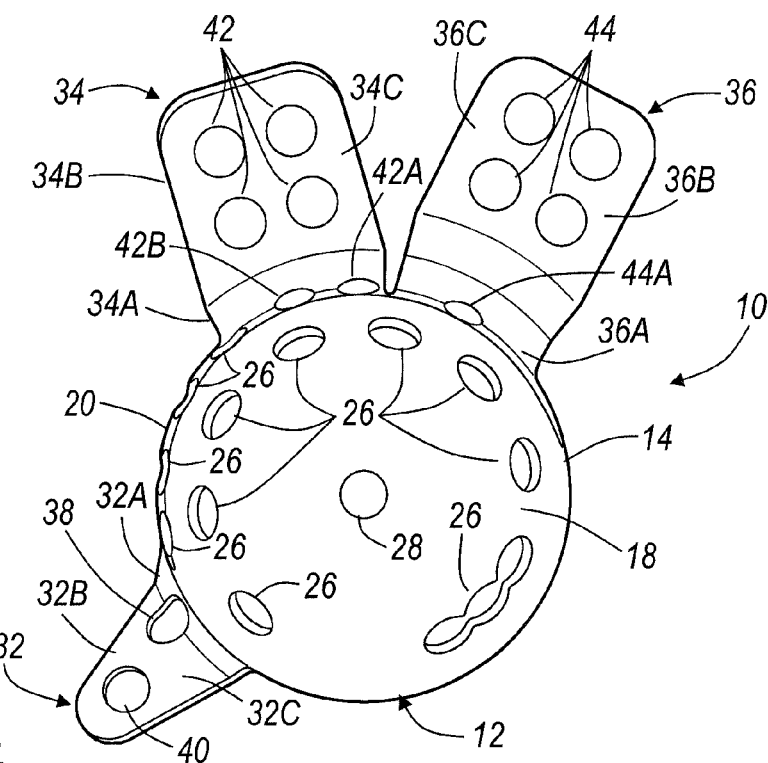
FIG. 4 is a rear plan view of an acetabular prosthesis, in accordance with one embodiment of the present invention.
Figure 5:
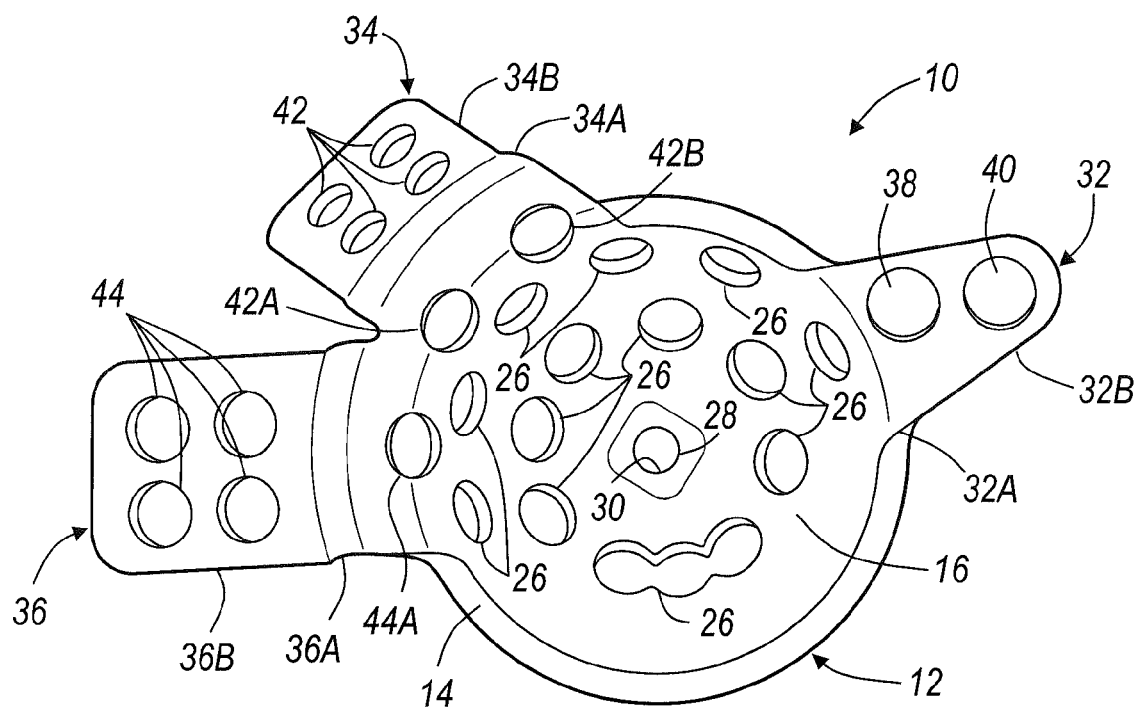
FIG. 5 is a front plan view of an acetabular prosthesis, in accordance with one embodiment of the present invention.
Figure 6:
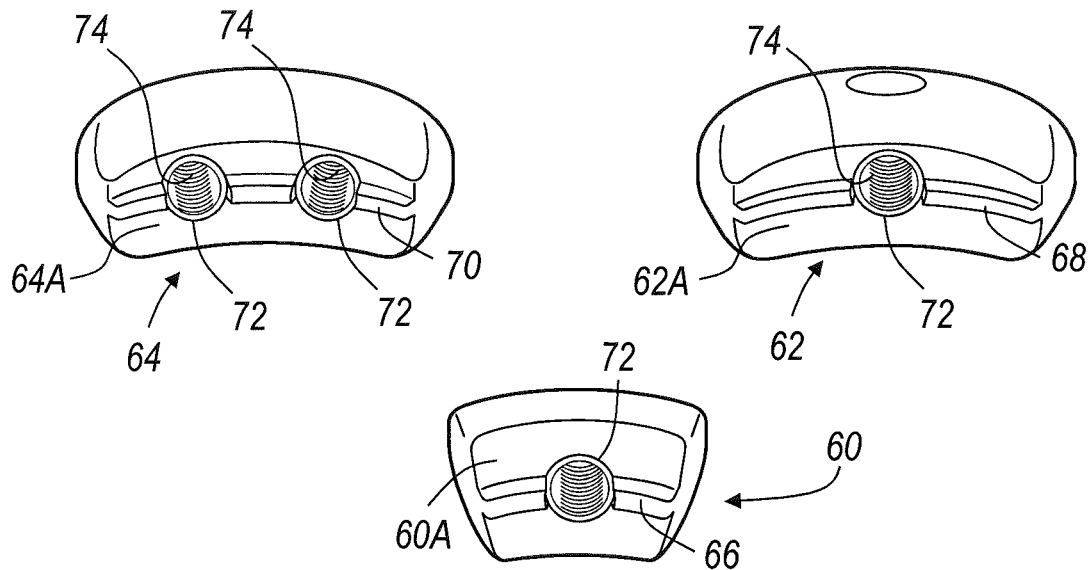
FIG. 6 is a side perspective view of several acetabular spacer members for an acetabular prosthesis, in accordance with one embodiment of the present invention.
Figure 7:
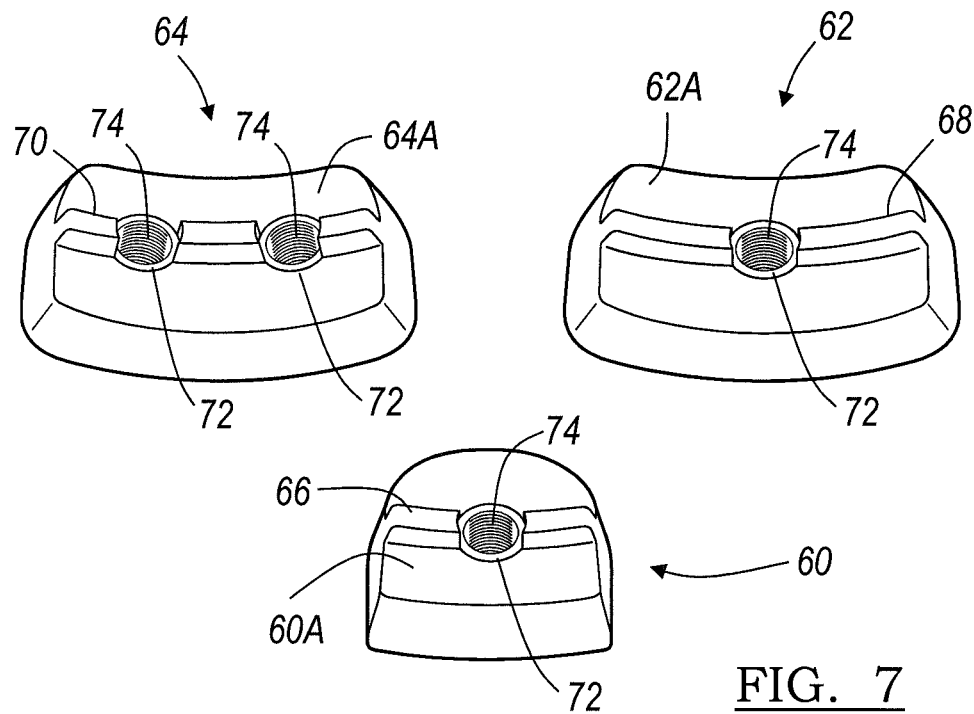
FIG. 7 is a bottom plan view of several acetabular spacer members for an acetabular prosthesis, in accordance with one embodiment of the present invention.
Figure 8:
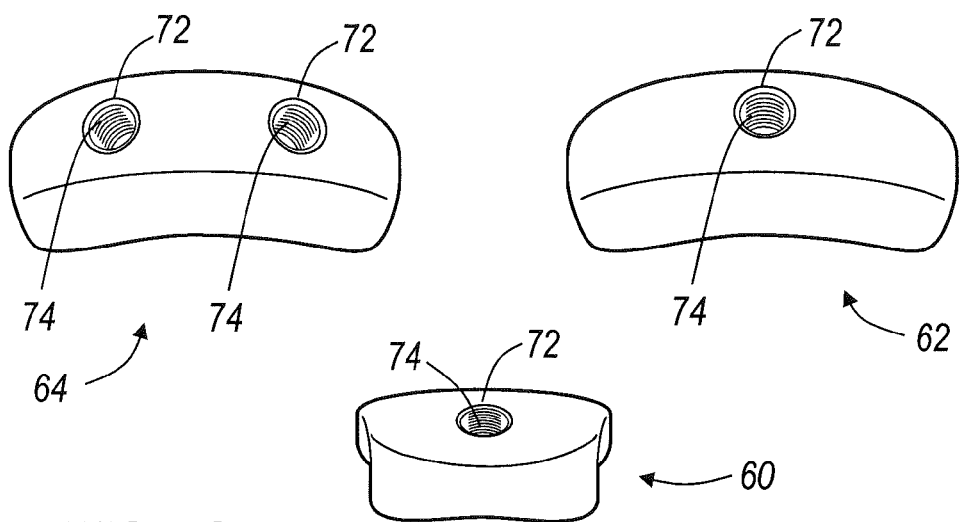
FIG. 8 is a top perspective view of several acetabular spacer members for an acetabular prosthesis, in accordance with one embodiment of the present invention.
Figure 9:
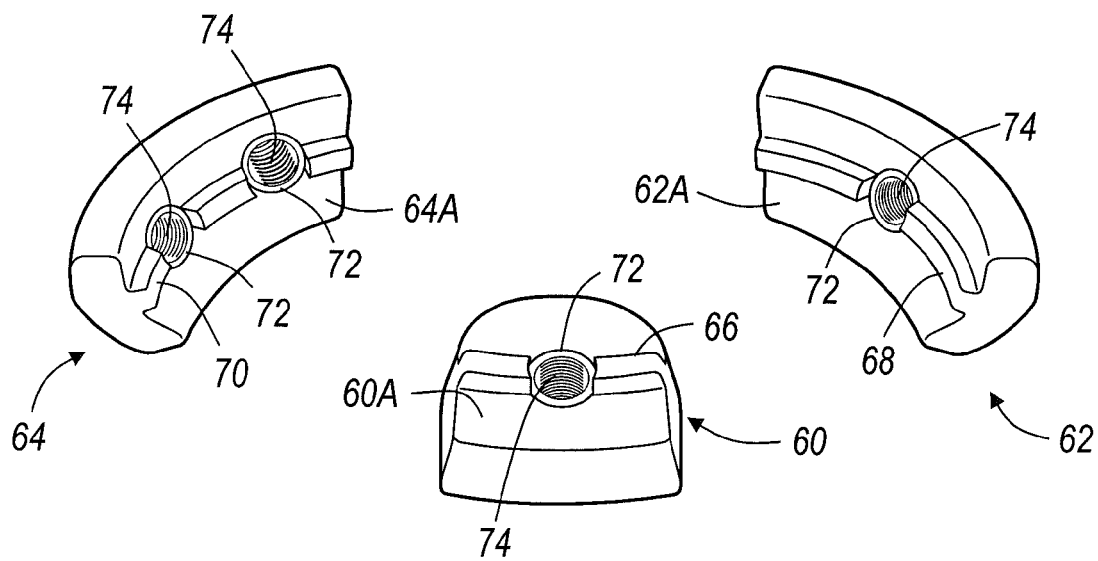
FIG. 9 is a bottom perspective view of several acetabular spacer members for an acetabular prosthesis, in accordance with one embodiment of the present invention.

The following description of the embodiments concerning a method and apparatus for providing a modular acetabular prosthesis for use in orthopedic surgical procedures, and trials therefore, are merely exemplary in nature and are not intended to limit the invention or its application or uses. Moreover, while the present invention is described in detail below with reference to performing a revision type implantation procedure, it will be appreciated by those skilled in the art, that the present invention is clearly not limited to only revision type orthopedic surgical procedures and may be used with various other orthopedic surgical procedures as well.

Referring to FIGS. 1-5, an acetabular prosthesis 10, according to a general embodiment, is shown. The acetabular prosthesis 10 includes a modified hemispherical acetabular cup 12. The acetabular cup 12 is said to be "hemispherical" in that it is not a perfect hemisphere; but rather, it includes an arcuate portion 14 extending along the periphery thereof without extending beyond the hemisphere of the acetabular cup 12.

The acetabular cup 12 is preferably constructed from any suitable biocompatible material, such as titanium, stainless steel, titanium alloy, cobalt-chrome-molybdenum alloy, and the like.

It should be noted that the acetabular cup 12 would normally also be associated with other components, such as a congruent shell or bearing liner (not shown) retained within the acetabular cup 12, via bone cement or a ring lock (not shown), which are not depicted for purposes of clarity.

The acetabular cup 12 preferably includes a substantially concave inner surface 16 and a substantially convex outer surface 18, wherein the outer surface 18 is operable to be received in the acetabulum. The inner surface 16 may be either roughened or smooth, whereas the outer surface 18 may be smooth or roughened with a grit blast or a porous surface layer (not shown) to facilitate bone tissue in-growth.

An area defining an optional receptacle or groove 20 is located in at least a portion of the outer surface 18 of the acetabular cup 12. The groove 20 may include tapered end portions 22, 24. The groove 20 is located in proximity to a peripheral surface of the acetabular cup 12, and generally in the superior and posterior region of the acetabular cup 12. The exact purpose of the groove 20 will be explained later in detail.

The acetabular cup 12 may include at least one, and generally, a plurality of throughbores 26 located therein. It should be noted that the groove 20 is bisected by at least one of the throughbores 26. The throughbores 26 provide a number of functions, such as enabling fastening members (not shown) to pass through the acetabular cup 12. Additionally, the throughbores 26 provide for the infiltration of bone cement to improve adhesion, as well as providing for new bone tissue in-growth. At least one of the throughbores 28 includes a threaded surface 30 thereon for receiving an insertion instrument (not shown) for properly aligning the acetabular prosthesis 10 within the acetabulum. Throughbore 28 also includes a recessed area 28A which permits the insertion instrument (not shown) to securely engage the acetabular cup 12 and permits controlled rotation of same. It will be noted that any graft material and/or bone cement should preferably be placed into the acetabulum before securing the acetabular cup 12 thereto.

A more specific description of the typical installation of an acetabular prosthesis can be found in U.S. Pat. Nos. 5,314,490; 5,326,367; 5,326,368; 5,702,477; 5,871,548; 5,931,870; and 6,162,257, the entire specifications of which are incorporated herein by reference.

The acetabular cup 12 preferably includes at least one, and more preferably, three substantially rigid attachment or extension members 32, 34, and 36 integrally formed with the acetabular cup 12 for fastening the acetabular prosthesis 10 to at least a portion of one or more surfaces of the pelvis (not shown), such as the ilium and/or the ischium. Preferably, attachment member 32 is used for attachment to the ischium, whereas attachment members 34 and 36 are used for attachment to various surfaces of the ilium (e.g., anterior and posterior).

Attachment member 32 is shown as being substantially triangularly shaped; however, it is envisioned that the shape may be altered to other configurations. It will be noted that attachment member 32 has two distinct portions, i.e., a first substantially curved portion 32A originating from, and contiguous with, the inner surface 16 of the acetabular cup 12, and a second substantially planar portion 32B extending out from, and angling away from, the first portion 32A. The curvature profile may be modified to meet any anatomical requirements.

Attachment member 32 preferably includes at least one, and more preferably, a plurality of throughbores located therein. In this view, a throughbore 38 is provided in the curved portion 32A and another throughbore 40 is provided in the planar portion 32B. The throughbores 38, 40 provide a number of functions, such as enabling fastening members such as a surgical screw (not shown) to pass therethrough in order to allow the fastening member 32 to be secured to the ischium.

Attachment member 34 is shown as being substantially rectangular shaped; however, it is envisioned that the shape may be altered to other configurations. It will be noted that attachment member 34 has two distinct portions, i.e., a first substantially curved portion 34A originating from, and contiguous with, the inner surface 16 of the acetabular cup 12, and a second substantially planar portion 34B extending out from, and angling away from, the first portion 34A. The curvature profile may be modified to meet any anatomical requirements.

Attachment member 34 preferably includes at least one, and more preferably, a plurality of throughbores 42 located therein. In this view, additional throughbores 42A and 42B are provided in the curved portion 34A. The throughbores 42, 42A, and 42B provide a number of functions, such as enabling fastening members such as a surgical screw (not shown) to pass therethrough in order to allow the fastening member 34 to be secured to at least a portion of a surface of the ilium.

Attachment member 36 is also shown as being substantially rectangular shaped; however, it is envisioned that the shape may be altered to other configurations. It will be noted that attachment member 36 also has two distinct portions, i.e., a first substantially curved portion 36A originating from, and contiguous with, the inner surface 16 of the acetabular cup 12, and a second substantially planar portion 36B extending out from, and angling away from, the first portion 36A. Again, the curvature profile may be modified to meet any anatomical requirements.

Attachment member 36 preferably includes at least one, and more preferably, a plurality of throughbores 44 located therein. In this view, an additional throughbore 44A is provided in the curved portion 36A. The throughbores 44 and 44A provide a number of functions, such as enabling fastening members such as a surgical screw (not shown) to pass therethrough in order to allow the fastening member 36 to be secured to at least another portion of a surface of the ilium spaced away from attachment member 34.

The installation of the acetabular prosthesis 10 would be accomplished in any number of ways, as are currently known in the art. The surgeon would surgically prepare the acetabulum and surrounding pelvic area to receive the acetabular prosthesis 10. This preparation would typically include removing any debris (e.g., bone fragments, bone cement) from the acetabulum. The surgeon would then install an allograft, if necessary, and install bone cement, if necessary, into the acetabulum. The acetabular cup 12 would then be received into, and anatomically aligned with, the acetabulum. At least one fastening member, such as a surgical screw, would then be placed through one of the throughbores 26 and into the interior of acetabulum, thus securing the acetabular cup 12 to the acetabulum. The attachment members 32, 34, and 36 would then be secured to the ischium and ilium, respectively, with fastening members, such as surgical screws.

However, if the acetabulum and/or the surrounding pelvic structures have any significant defects present, the loading will be borne primarily by the allograft and/or bone cement material, as previously described. Therefore, it is desirable to have the surfaces of the acetabular prosthesis 10 actually abut against the respective surfaces of the acetabulum and/or the surrounding pelvic structures, as opposed to using allografts and bone cement to fill the gap therebetween. Because the acetabular prosthesis 10 is constructed of metallic material, it is much stronger than allografts and bone cement, and therefore is much more able to withstand the loads and forces associated with standing, walking, and running activities.

Therefore, the present invention may employ at least one augment or spacer member to compensate for the fact that the acetabulum and/or the surrounding pelvic structures may have defects therein which prevent the outer surface 18 of the acetabular cup 12 from contacting the surface of the acetabulum, and/or the outer surfaces 32C, 34C, and 36C, respectively, from contacting the respective surfaces of the pelvis, i.e., the ischium and the ilium.

The spacer members are preferably constructed from any suitable biocompatible material, such as titanium, stainless steel, titanium alloy, cobalt-chrome-molybdenum alloy, etc. and is preferably made of the titanium alloy Ti-6Al-4V.

Referring to FIGS. 6-9, several different types of acetabular spacer members 60, 62, and 64 for use with the outer surface 18 of the acetabular cup 12, according to the general teachings of the present invention, are shown. It should be noted that only one spacer member would generally be used at a time in practice; however, multiple spacer members may be used in some instances. For example, if there is a relatively small defect in the superior region of the acetabulum, acetabular spacer member 60 can be employed. If there is a larger defect, either acetabular spacer member 62 or 64 may be used. It is envisioned that either smaller and/or larger acetabular spacer members may also be employed with the present acetabular prosthesis.

The acetabular spacer members 60, 62, and 64 may be substantially curved so that the lower surfaces 60A, 62A, and 64A, substantially conform to the curvature of the outer surface 18 of the acetabular cup 12. Additionally, the acetabular spacer members 60, 62, and 64 may include an area defining a substantially curved and raised appendage or ridge 66, 68, and 70 formed on the lower surface 60A, 62A, and 64A, respectively, thereof for mating, and more preferably, sliding engagement with the groove 20. Finally, each acetabular spacer member 60, 62, and 64 preferably has at least one throughbore 72. The throughbores 72 preferably include a threaded surface 74 thereon. It should be noted that the raised ridges 66, 68, and 70 are bisected by the respective throughbore 72.

The purpose of the raised ridges 66, 68, and 70, respectively, is to allow the respective acetabular spacer member 60, 62, or 64 to slidingly mate with the groove 20 on the outer surface 18 of the acetabular cup 12. This allows the surgeon the option of positioning the respective acetabular spacer member 60, 62, or 64 practically anywhere along the length of the groove 20 to best deal with the particular acetabular defect in the superior-posterior region. For example, the acetabular spacer member 60, 62, or 64 can slide in a superior-posterior direction with respect to the acetabulum. It is also envisioned that the acetabular spacer member 60, 62, or 64 can slide in a medial direction, as well. Once the final position of the acetabular spacer member is determined, the surgeon can then secure the respective acetabular spacer member to the acetabular cup 12 by inserting a fastening member, such as a surgical screw, through one or more available throughbores 72 which generally aligns with one or more of the throughbores 26 which bisect the groove 20. The screw may extend upwardly through the acetabular cup 12 and into the respective acetabular spacer member, with the screw tip not extending past the upper surface of the respective acetabular spacer member. The modified acetabular prosthesis 10 can then be installed in the acetabulum, as previously described, such that the acetabular spacer member 60, 62, or 64 is disposed between the outer surface 18 of the acetabular cup 12 and the acetabulum.

Unfortunately, the use of acetabular spacer members 60, 62, or 64 alone is sometimes not enough to address each and every particular clinical situation. The use of the acetabular spacer members 60, 62, or 64 may address the defect in the acetabulum, but it may not address a defect in the surrounding pelvic structures, or alternatively, the use of the acetabular spacer members 60, 62, or 64 may alter the attachment point of the attachment members 32, 34 or 36 such that an undesirable gap is created between the respective outer surfaces 32C, 34C, and 36C and the pelvis.

Therefore, the present invention employs at least one other augment or spacer member to compensate for the fact that the surrounding pelvic structures may have defects therein which prevent the outer surfaces 32C, 34C, and 36C of rigid attachment members 32, 34, and 36, respectively, from contacting the respective surfaces of the pelvis, i.e., the ischium and the ilium.

Figure 10:
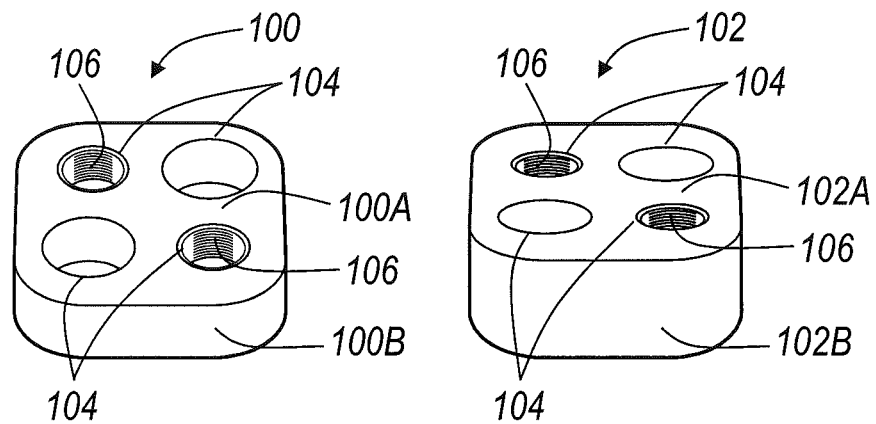
FIG. 10 is a front perspective view of two attachment spacer members for an acetabular prosthesis, in accordance with one embodiment of the present invention.
Figure 11:
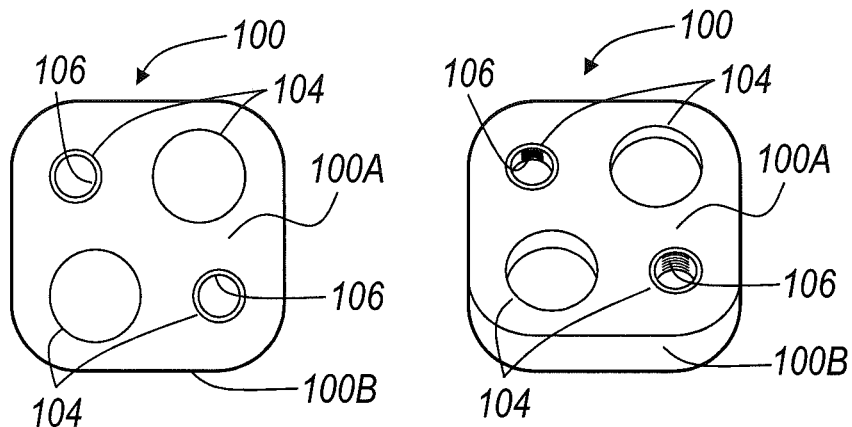
FIG. 11 is a top plan view of two attachment spacer members for an acetabular prosthesis, in accordance with one embodiment of the present invention.
Figure 12:
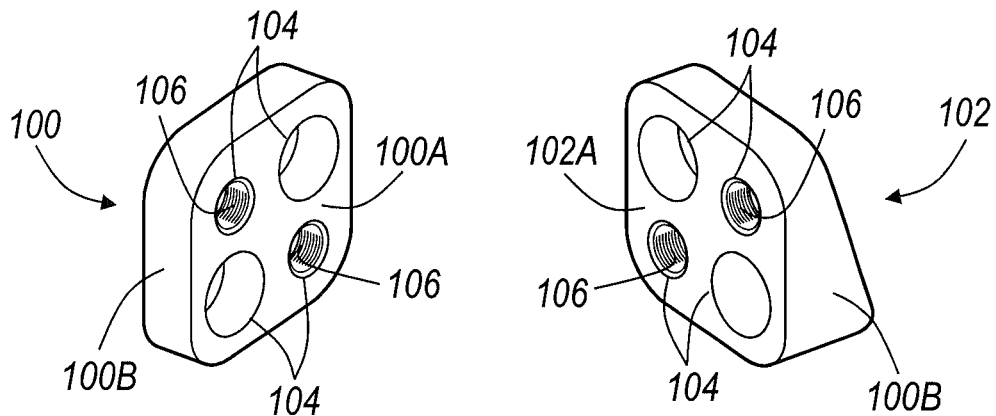
FIG. 12 is a side perspective view of two attachment spacer members for an acetabular prosthesis, in accordance with one embodiment of the present invention.

Referring to FIGS. 10-12, two different types of attachment spacer members 100 and 102 for use with the attachment members 32, 34, and 36, respectively, according to the general teachings of the present invention, are shown. It should be noted that more than one attachment spacer member can be used at one time in practice. For example, if there is a relatively small defect in the surface of the ischium, or attachment member 32 can not abut it, an attachment spacer member 100 or 102 can be employed. If there is a defect in the surface of the ilium (either anterior and/or posterior), or attachment member 34 or 36 can not abut it, an attachment spacer member 100 or 102 can be employed. It is envisioned that either smaller and/or larger attachment spacer members may also be employed with the present invention.

The attachment spacer members 100 and 102 generally have at least one flat surface 100A and 102A, respectively, for mating adjacently against the planar portions 32B, 34B, and 36B of attachment members 32, 34, and 36, respectively. The other surface of the attachment spacer members 100 and 102 may be either flat and parallel 100B or flat and non-parallel (i.e., inclined) 102B.

Each attachment spacer member 100 and 102 may have at least one throughbore 104. At least one of the throughbores 104 generally includes a threaded surface 106 thereon. The surgeon can then secure the respective attachment spacer member 100 or 102 to the outer surface 32C, 34C, or 36C, respectively, by inserting a fastening member, such as a surgical screw, through one or more available throughbores 104 which preferably aligns with one or more of the throughbores 40, 42, 44, respectively, in planar portions 32B, 34B, or 36B, respectively. The further modified acetabular prosthesis 10 then can be installed in the acetabulum, as previously described, such that the attachment spacer members 100 and/or 102 are disposed between the outer surface 32C, 34C, or 36C, respectively, of the planar portions 32B, 34B, or 36B, respectively, of the attachment members 32, 34, or 36, respectively, and the pelvis, i.e., the ischium and/or the ilium. Preferably, two diagonally opposed and spaced throughbores 104 are used to attach the attachment spacer member 100 and 102 to the outer surface 32C, 34C, or 36C, respectively, of the planar portions 32B, 34B, or 36B, respectively, of the attachment members 32, 34, or 36, respectively, and the pelvis, i.e., the ischium and/or the ilium. Bone screws (not shown) can then be inserted through the two diagonally opposed throughbores 104, and the aligned one or more of the throughbores 40, 42, 44, respectively, to secure the attachment members 32, 34, or 36, respectively, to the pelvis.

It should be noted that sometimes it is only necessary to use the attachment spacer members 100 and/or 102 alone, instead of using them in conjunction with an acetabular spacer member 60, 62, or 64. In that scenario, it is beneficial that the groove 20 is employed in the outer surface 18 of the acetabular cup 12, as opposed to a raised appendage or ridge which may interfere with the proper alignment of the acetabular cup 12, or might irritate the acetabulum.

Although the acetabular prosthesis 10, also referred to as a protrusio cage or protrusio acetabular prosthesis, may be implanted using any number of methods, the acetabular prosthesis 10 is generally implanted after employing a particular trialing prosthesis. The trialing acetabular prosthesis generally resembles the acetabular prosthesis 10, but may be constructed out of a less substantial material than the acetabular prosthesis 10. The trial acetabular prosthesis may also differ from the acetabular prosthesis 10 by not having a porous coat or as many throughbores. The trialing acetabular prosthesis allows the acetabular prosthesis to be placed in the acetabulum to assure a proper size and fit before attempting to secure the acetabular prosthesis 10 to the pelvic area. In addition, a trialing acetabular prosthesis allows the physician to determine the appropriate spacers, if necessary, or a slightly augmented orientation of the various attachment members 32, 34, and 36. Moreover, trial attachment members may be bent or deflected to determine if the attachment members 32, 34, and 36 should also be bent before implantation.

Figure 20:
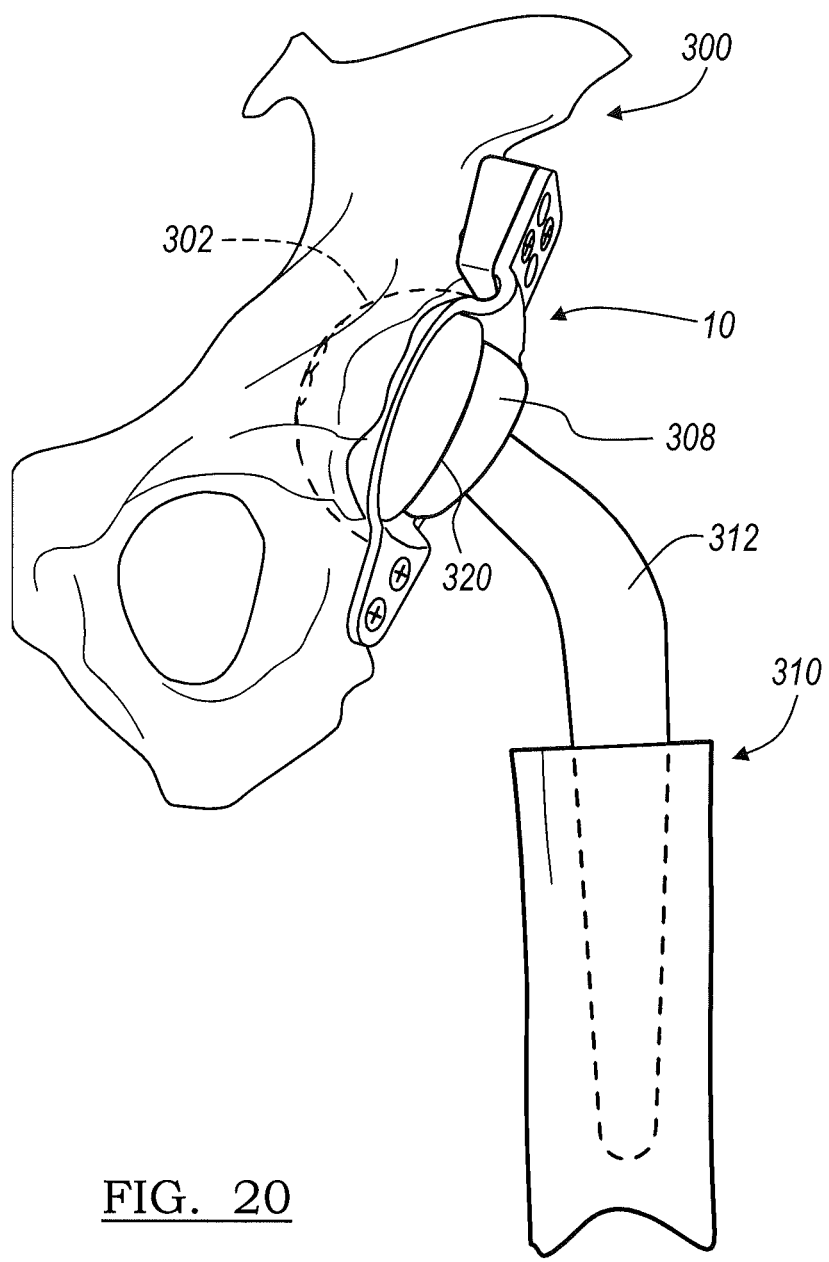
FIG. 20 is a perspective view of the protrusio cage and a cup being implanted after the trialing has occurred.
Figure 21:
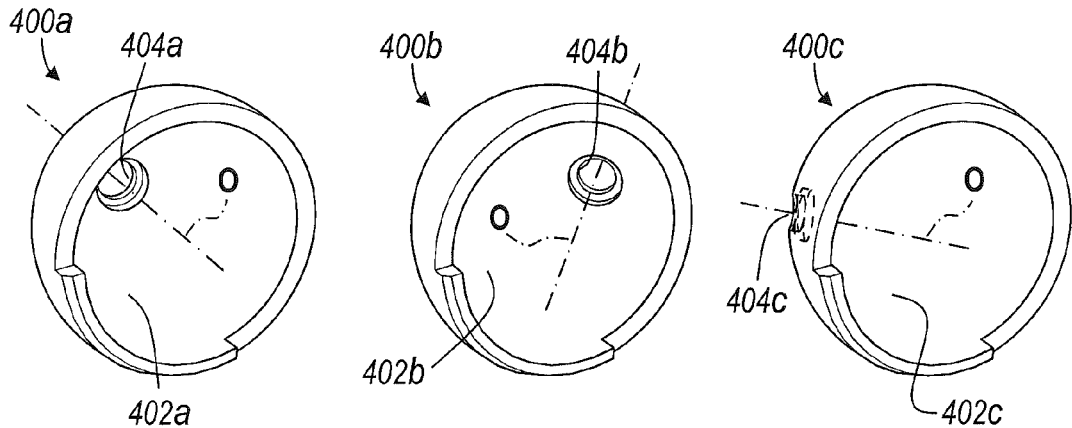
FIG. 21 is a perspective view of a series of trial shells according to an alternate embodiment.

Not only may a trialing component be provided for the acetabular prosthesis 10, but a trial shell or bearing liner 200 may also be provided. The trial shell 200 may be associated with the acetabular prosthesis 10 after it has been implanted to trial the appropriate position of the prosthetic shell (at 320 in FIG. 20) before implanting the prosthetic shell. The prosthetic shell, substantially resembles the trial shell 200, save that the prosthetic shell is substantially solid and continuous.

With reference to FIGS. 13-15, the trial shell 200 generally include a shell that is substantially congruent to the acetabular cup 12 of the acetabular prosthesis 10. Thus, the trial shell includes an exterior 201 that is substantially convex that is substantially congruent with the acetabular cup 12. The trial shell 200 also includes an internal or shell recess 202, which is designed to substantially mate with either the ball of a femoral prosthetic or the head of a natural femur. Between the inner recess 202 and the exterior 201, and at a meridian of the trial shell 200, is a surface or wall 203. A raised ridge 203a may be provided on a portion of the wall 203.

Formed in and along an arc of the exterior 201 is a trial track or trial slot 204. The slot 204 passes substantially through the trial shell 200 and provides a passage from the exterior 201 to the internal recess 202. The slot 204 may reach substantially from a first side 205 to a second side 206 of the interior recess 202. The slot 204 provides a channel that reaches substantially across the trial shell 200. The slot 204 generally defines a total arc about 60° to about 120°. Therefore, the trial shell 200 may have a range of motion of about 60° to about 120°. It will be understood that various different trial shells may include an arc having a different angle. The slot 204 is an orientation portion of the trial shell 200, as described further herein. The slot 204 provides an area for a trial screw 212 to be received. Furthermore, a depression or countersink 208 substantially surrounds the perimeter of the slot 204.

The trial screw 212 would generally include a head portion 214 and a threaded shank 216. The head portion 214 may define a substantially arcuate top portion 218. The head portion 214 is substantially received or is nested in the countersink 208. After placing the screw 212 into the trial shell 200, the screw 212 would not interfere with a head or ball portion of a femur (illustrated in FIG. 19a-19c) since the head 214 rests within the countersink 208. The shank portion 216 is received through the slot 204 and may be held in place with a lock ring 217 or similar appropriate device. The trial shell 200, trial screw 212, and lock ring 217 form an assembly easily manipulated by a physician and eliminates a non-affixed component during the procedure. Once received through the slot 204, the threaded shank 216 may engage the threads 30 of the throughbore 28. The trial screw 212, when received through the slot 204 and tightened into the threads 30, would substantially not interfere with the inner recess 202. As mentioned above, the top portion 218 of the head 214 further defines the inner recess 202 or is substantially congruent therewith, such that when a head portion or ball portion of a hip prosthesis is inserted into the inner cup 202, the trial screw 212 does not interfere with movement of the head portion.

Figure 16:
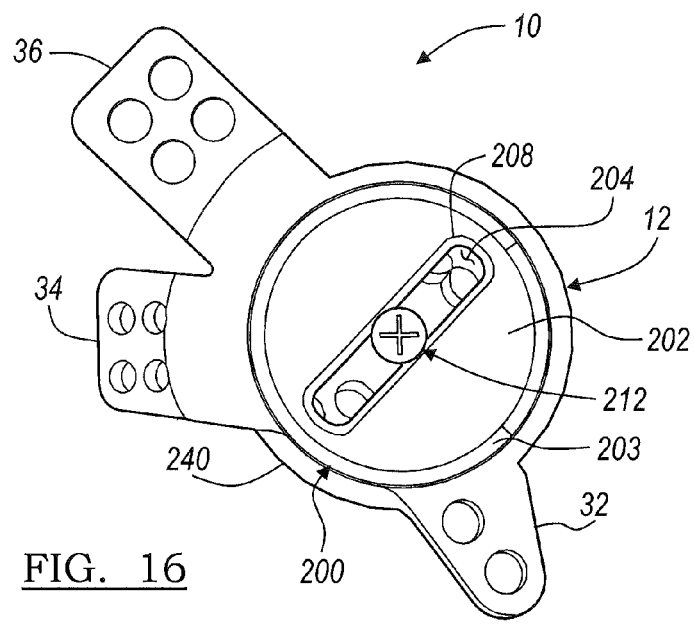
FIG. 16 is an elevated view of the trial cup held within a protrusio cage.

With reference to FIG. 16, once assembled, the trial shell 200 may be affixed substantially fixed and motionless relative the acetabular cup 12. This is accomplished by passing the trial screw 212 through the slot 204 of the trial shell 200 and engaging the threads 30 with the trial screw 212. The trial screw 212 may then be tightened against the recess 208, formed in the trial shell 200, to hold the trial shell 200 in a predetermined fastened position. In this position, the trial shell 200 is substantially immobile relative the acetabular cup 12. The trial screw 212 interacts with the threads 30 to provide an attachment or connection mechanism between the trial shell 200 and the acetabular cup 12. It will be understood, however, that other connection mechanisms may provide similar connections. For example a pin or removable rivet may be used to selectively fix the trial shell 200 in a selected orientation relative the acetabular cup 12.

The trial screw 212 may be loosened so that the trial shell 200 may be moved or adjusted defining a locating position and then reaffixed to the fastened position by tightening the screw 212 against the recess 208 of the trial shell 200. It will be understood that other appropriate shapes or types of screws may be used as the trial screw 212. Furthermore, any appropriate tool may be used to manipulate the trial screw 212.

Figure 17A:
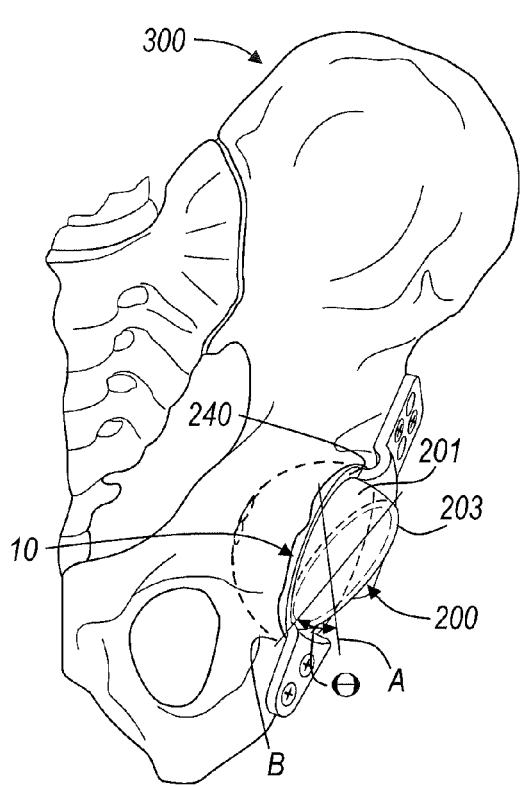
FIG. 17A is a perspective view of a protrusio cage implanted in an acetabulum and a trialing cup in a first position.
Figure 17B:
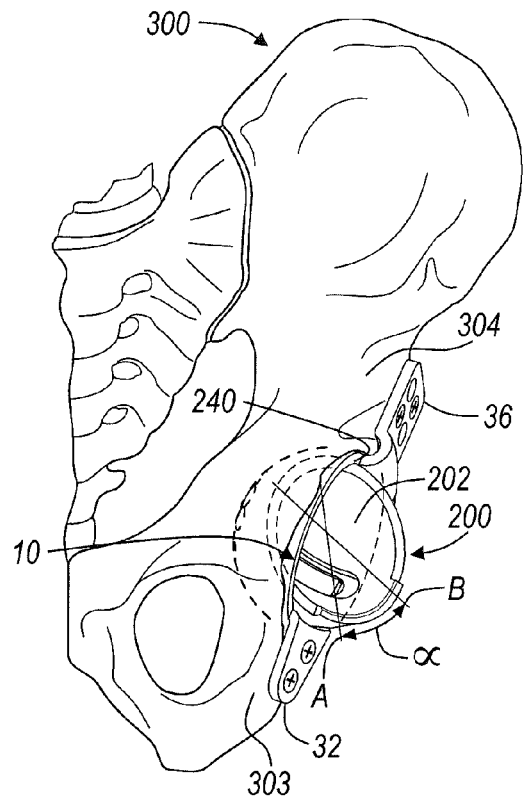

With reference to FIGS. 17a and 17b, the trial shell 200 may be positioned and fixed at a substantial plurality of orientations relative the acetabular prosthesis 10. For discussion purposes, the following axes are defined, nevertheless it will be understood that different references may provide different angles, but this will not alter the present discussion. A rim 240 of the acetabular cup 12 defines an acetabular cup plane A. The rim 203 of the trial shell 200 also defines a plane B. A third axis or axis of orientation C is defined by the shank 216 of the trial screw 212. It will be understood that the trial shell 200, when the trial screw 212 is loosened, may be moved along the slot 204 for its length and rotated substantially 360° around the trial screw 212. The various orientations of the trial shell 200 are relative the orientation axis C. The orientation axis C is also substantially defined by the throughbore 28 which is formed substantially at a pole of the acetabular cup 12.

One exemplary position will allow a negative angle θ, specifically illustrated in FIG. 17a. The angles given are in reference to the relative orientation of the planes A and B when in a pelvis 300. Particularly, the relative orientation of the interior portion of the plane B relative to plane A. Therefore, when the angle θ is negative the trial shell plane B is below acetabular cup plane A. In this exemplary position, the trial screw 212 may be tightened to hold the trial shell 200 in place. With reference to FIG. 17b, a separate or different exemplary orientation may provide a positive angle α. It will be understood that these are merely exemplary of the many plurality of orientations the trial shell 200 may have relative the acetabular prosthesis 10 by loosening the trial screw 212 and moving the trial shell 200 relative the acetabular prosthesis 10. This allows the trial shell 200 to be orientated for trialing of the femur before fixedly implanting the prosthetic shell into the acetabular cup 12 after implanting the acetabular prosthesis 10.

Figure 18:
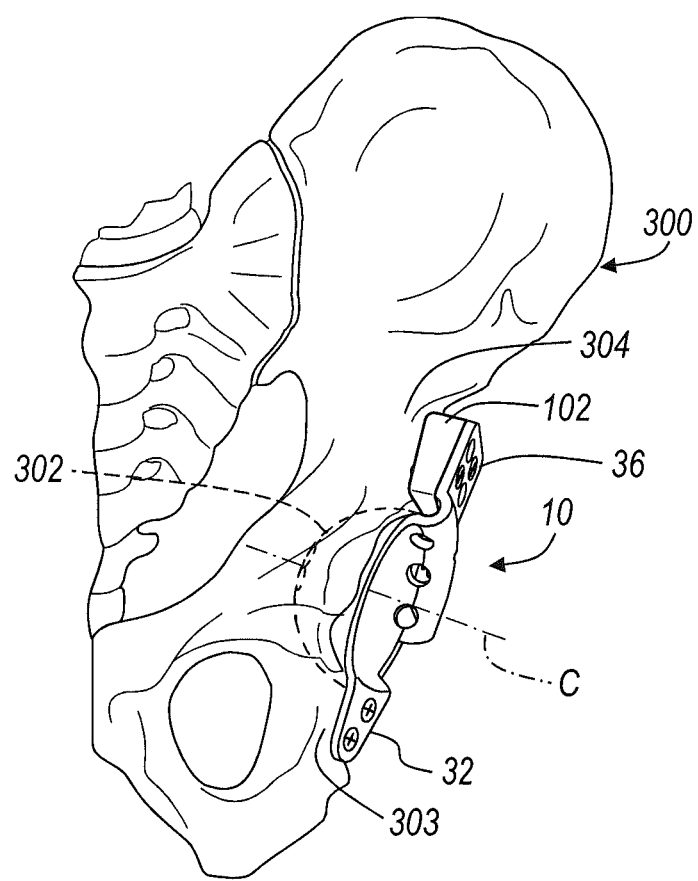
FIG. 18 is an elevational view of a protrusio cage and implanted in an acetabulum and a trialing cup held therein.

An exemplary method for using this system as disclosed herein, provides a method to both trials the acetabular prosthesis 10, with a trial acetabular prosthesis or protrusio cage, and to trial the trial shell 200 for the prosthetic liner 320. Initially, however, an acetabulum 302 is prepared as generally known in the art, and generally includes removing any extraneous cartilage, loose bone debris or other material that would interfere with the implantation of the acetabular prosthesis 10. After properly preparing the acetabulum 302, a trial acetabular prosthesis or trial protrusio cage can be trialed in the prepared acetabulum 302. As discussed above, the trial acetabular prosthesis is substantially similar to the acetabular prosthesis 10 save that it may have a smooth outside as opposed to a porous coat and other minor differences. The trial acetabular prosthesis will help the physician determine the proper implant size and placement of any necessary spacers or if any of the attachment members need to be repositioned, as by bending, before implanting the acetabular prosthesis 10. The physician may also determine a proper orientation using the trial acetabular prosthesis which is then mimicked when implanting the acetabular prosthesis 10. Once the physician has trialed the placement of the acetabular prosthesis 10, the appropriate spacers may be assembled and the proper orientation of the acetabular prosthesis 10 is easily determined. Then, the assembled components are implanted into the acetabulum 302 of the patient, including the acetabular prosthesis 10 in the appropriate orientation and the appropriate and necessary spacers, as illustrated in FIG. 18. The acetabular prosthesis 10 may be implanted using any appropriate methods such as using fastening members such as screws, or other fixation means such as bone cement. The attachment members 32, 34, and 36 are also affixed to the appropriate portions of the ilium 303 and ischium 304 of the pelvis 300.

After the acetabular prosthesis 10 has been affixed in place, the trial shell 200 may be positioned in the acetabular cup 12 by placing the trial screw 212 through the slot 204 and engaging the threads 30 of the throughbore 28. Although the orientation axis C may be slightly different depending upon the individual into which the acetabular prosthesis 10 is implanted, the orientation axis C is generally does not lie on either the median plane or coronal plane of the patient. The trial shell 200 is oriented relative this orientation axis C by moving it along the slot 204 of the trial shell 200, as described above.

After the acetabular prosthesis 10 is implanted into the acetabulum, a first orientation of the trial shell 200 is chosen. The physician implanting the acetabular prosthesis 10 chooses a first orientation by placing the trial shell 200 at a desired orientation relative the acetabular cup 12 and fixing it in place by tightening the trial screw 212 against the recess 208 of the trial shell 200. After this occurs, the physician can determine whether an appropriate orientation has been chosen to allow range of movement for the hip joint. This is done by placing the head 308 of the femur 310 in place in the interior recess 202. The femur 310 is then moved through an appropriate range of motion to determine if the stem or neck 312 of the femur 310 engages any portion of the trial shell 200. It is generally desired to have a low or substantially no dislocation force when the femur 310 is moved through a general range of motion. If such a force were to occur the head 308 may dislocate from the inner recess 202. It will be understood that the head 308 may be a prosthetic head, a natural head, or a femoral replacement.

Figure 19A:
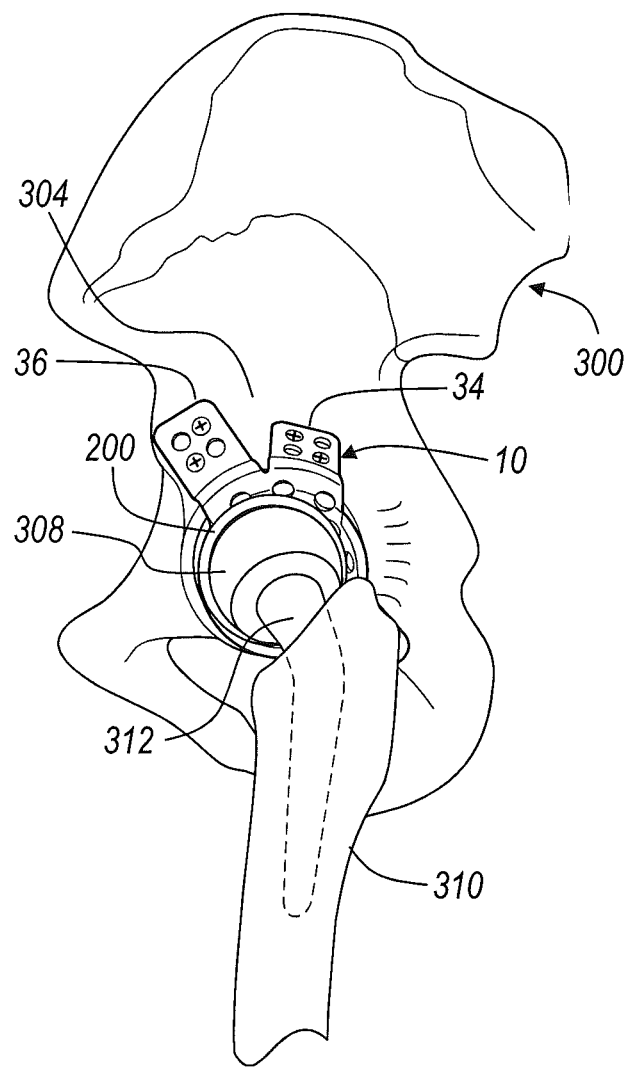
FIGS. 19A-19C illustrate a trial of the range of motion of a hip joint after the trialing cup has been affixed in a first trialing orientation.
Figure 19B:
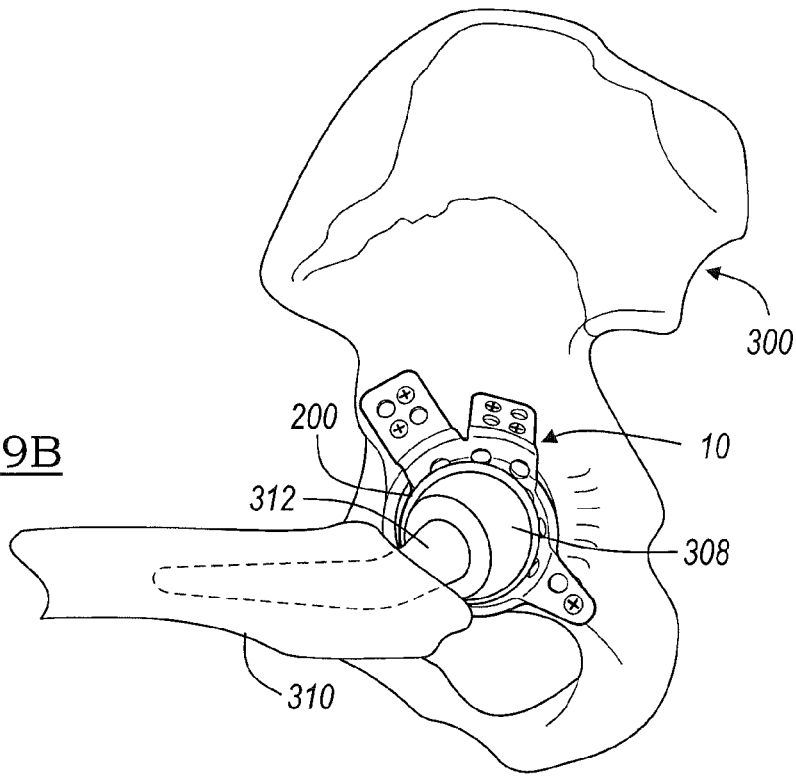
Figure 19C:
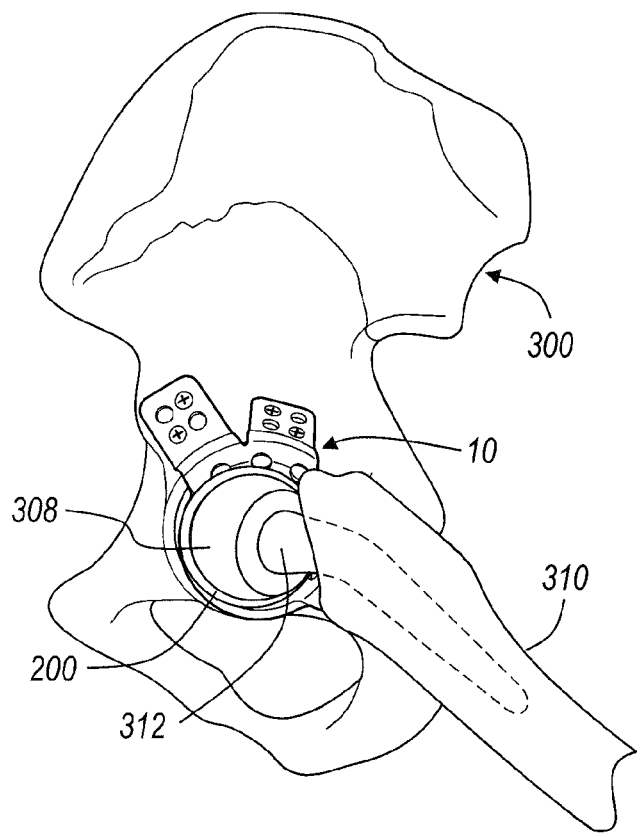

With reference to FIG. 19A, the femur 310 may first be moved to a natural or neutral position. With reference to FIG. 19B, the femur may then be moved to about 90° of flexion and taken through a range of internal rotation. And finally with reference to FIG. 19C, the femur may be moved to about 30° of extension and taken through a range of external rotation. It will be understood the femur 310 is generally moved fluidly and continuously from position to position. Also, a plurality of other specific positions may be trialed. In any of these positions, a contact between the femur 310 and the trial shell 200 may be felt or seen by the physician. Furthermore, a dislocation of the head from the trial shell 200 would also be ascertained. If the physician determines that the neck 312 of the femur 310 or the femur itself engages or contact a portion of the trial shell 200; or if the head 308 dislocates from the inner recess 202, the physician may attempt a different position of the trial shell 200. The trial shell 200 may be moved by first loosening the trial screw 212 moving the trial shell 200 to a different orientation, exemplarily illustrated in FIG. 17a or 17b, and retightening the trial screw 212 to hold the trial shell 200 substantially fixed in the new position. The physician may then trial the hip joint by moving the femur 310 again through a range of motion to determine whether any portion of the femur 310 engages a portion of the trial shell 200 or if the head 308 dislocates from the trial shell 200.

When the physician determines the proper orientation has been selected, the physician may then note the orientation and position of the trial shell 200. This may be done through any appropriate method, such as marking the orientation on the trial shell 200 or noting the orientation of the trial shell 200. The trial shell 200 may also include demarcations on the exterior 201. These demarcations may be noted when the orientation of the trial shell 200 is selected. Similar demarcations may be included on the exterior of the prosthetic shell 320 and may be used to match the orientation of the prosthetic shell 320 to the selected orientation. Alternatively the demarcations may provide a reference for placing the prosthetic shell 320.

Therefore, after the appropriate orientation is selected, the femur 310 is again dislocated from the inner recess 202 and the trial screw 212 and trial shell 200 are removed from the acetabular prosthesis 10. This is performed by simply removing the trial screw 212 and then removing the trial shell 200 from the acetabular prosthesis 10. After this occurs, a prosthetic shell or liner 320 may be implanted into the acetabular prosthesis 10. The prosthetic shell 320 is placed into the acetabular prosthesis 10 according to the determined orientation of the trial shell 200. It will be understood, therefore, that the trial shell 200 and the prosthetic shell 320 generally are similar in size and shape. Although the trial shell 200 may differ if the differences are accounted for in the procedure, such as offset or roundness of the trial shell 200 compared to the prosthetic liner 320. The prosthetic shell 320 is then permanently affixed in place using an appropriate means, such as a bone cement. The bone cement substantially permanently affixes the prosthetic shell 320 in place, such that after the femur 310 is placed to engage the prosthetic shell 320, the shell 320 does not move.

Therefore, a proper orientation of the shell 320 may be determined before the shell 320 is implanted into the acetabular prosthesis 10. The trial shell 200 allows a selection of a proper orientation of the shell 320 using a removably fixation means, such as the trial screw 212. This allows the physician to trial several orientations of the trial shell 200 before permanently affixing, or substantially permanently affixing a shell 320 into the acetabular prosthesis. Therefore, the appropriate orientation of the shell can be determined more precisely and with substantially little error by using the trial shell 200.

Turning now to FIGS. 21-25, the present invention according to an alternate embodiment incorporating a series of trial shells 400a-400c will be described. In this embodiment, the series of trial shells 400a-400c are used in place of the trial shell 200. Each trial shell 400a-400c includes an inner surface 402a-402c having an attachment device or passage 404a-404c thereon for accepting the trial screw 212. Each attachment passage 404a-404c of each trial shell 400a-400c is located at a unique location on the surface 402a-402c thereof. As will be described in greater detail, the unique placement of each attachment passage 404a-404c allows a selected trial shell 400a-400c to be located at a distinct angle with respect to the acetabular prosthesis 10 in a fastened position. Each trial shell 400a-400c is movable in one degree of freedom about an orientation axis O defined by the attachment passage 404a-404c.

Figure 22:
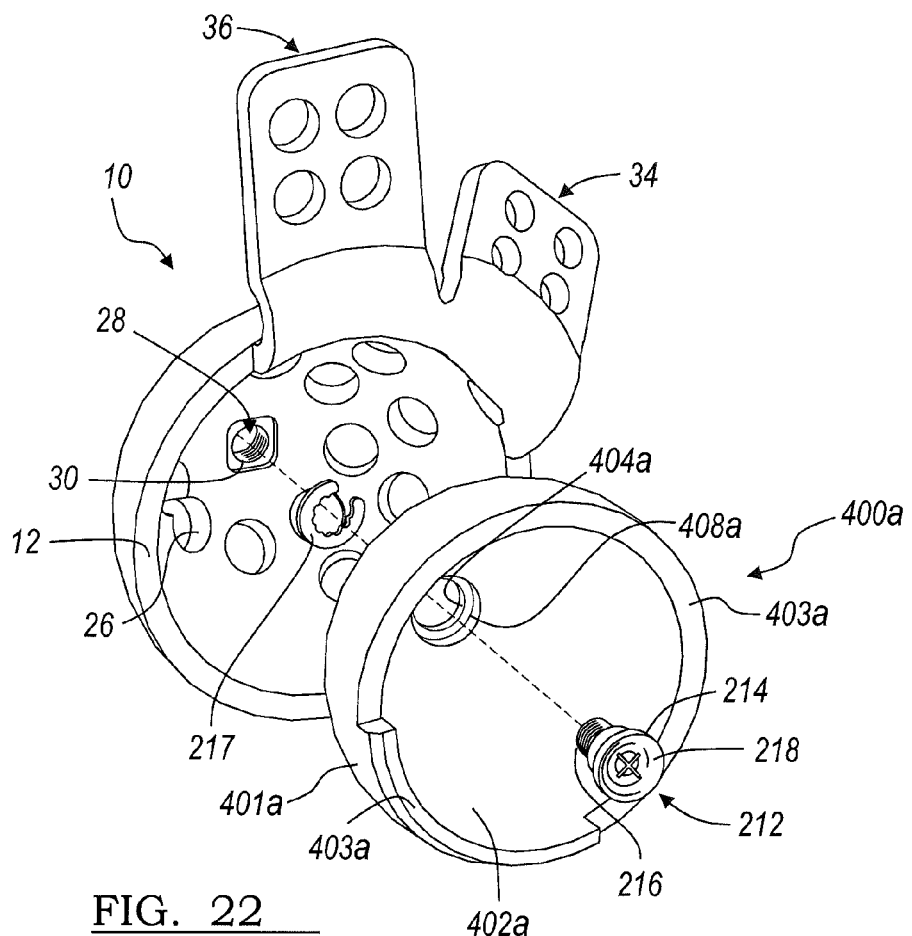
FIG. 22 is an exploded perspective view of one of the trial shells and a protrusio cage.

With specific reference to FIG. 22, the trial shell 400a generally includes a shell that is substantially congruent to the acetabular cup 12 of the acetabular prosthesis 10. As shown, the features of trial shell 400a are designated with similar reference numerals from those associated with trial shell 200 and include a 400 prefix. The trial shell 400a includes an exterior 401a that is substantially convex and congruent with the acetabular cup 12. The trial shell 400a also includes an internal or shell recess 402a designed to substantially mate with either the ball of a femoral prosthetic or the head of a natural femur. Between the inner recess 402a and the exterior 401a, and at a meridian of the trial shell 400a, is a surface or wall 403a. A raised ridge 403a may be provided on a portion of the wall 403a. Passage 404a is further defined by a countersink 408a for receiving the head portion 214 in a fastened position. Accordingly, after placing the screw 212 into the trial shell 400a, the screw 212 will not interfere with a head or ball portion of the femur.

Figure 23:
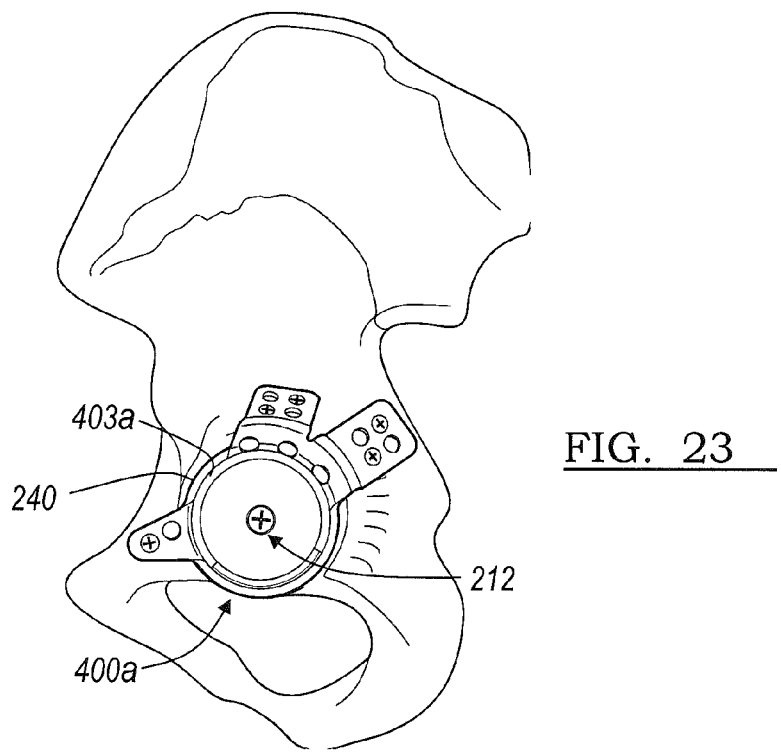
FIG. 23 is an elevated view of the trial cup of FIG. 22 held within a protrusio cage.

With reference to FIG. 23, the trial shell 400a is shown in a fastened position with the acetabular cup 12. The location of passage 404a on the surface 402a of the trial shell 400a is generally centralized or, more specifically, the orientation axis O extends through a centerpoint of a radius defined by the wall 403 of the trial shell 404a. As a result, the wall 403a of the trial shell 400a is substantially flush to the rim 240 of the acetabular cup 12 in a fastened position. In the locating position, the acetabular cup 400a is moveable in one degree of freedom about the trial screw 212 and the orientation axis O.

Figure 24:
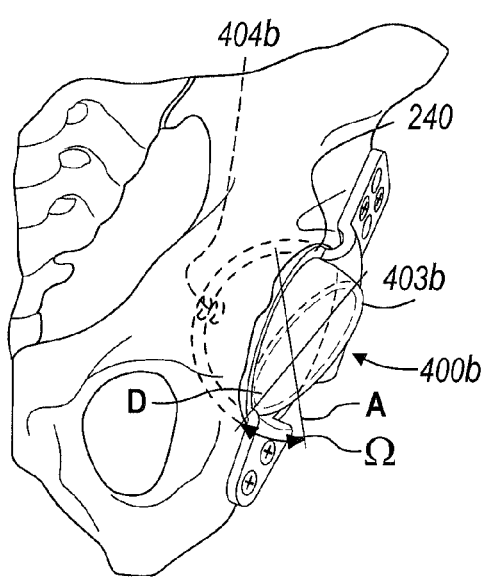
FIG. 24 is a perspective view of a protrusio cage implanted in an acetabulum and a first trialing cup in a first position.
Figure 25:
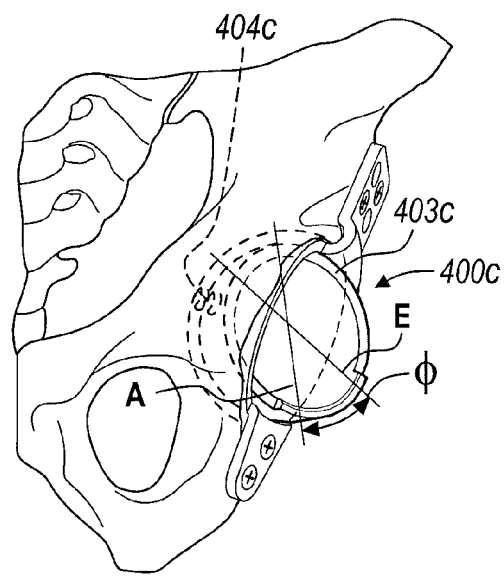
FIG. 25 is a protrusio cage implanted in an acetabulum and a second trialing cup in a second position different from that illustrated in FIG. 24.

Referring now to FIGS. 24 and 25 the trial shells 400b and 400c will be described in a fastened position. The trial shell 400b is shown received by the acetabular cup 12 in FIG. 24. A rim 403b of the trial shell 400b defines a plane D. As shown, the trial shell 400b is positioned at a negative orientation angle Ω defined between the respective planes A and D. Again, the trial shell 400b is rotatable in one degree of freedom about the trial screw (not specifically shown).

In FIG. 25, the trial shell 400c is shown received by the acetabular cup 12. A rim 403c of the trial shell 400c defines a plane E. The trial shell 400c is positioned at a positive orientation angle φ defined between the respective planes A and E. The trial shell 400c is rotatable in one degree of freedom about the trial screw. It is appreciated that alternative attachment passage locations may be provided on the trial shells 400a-400c. In addition, an alternate amount of trial shells may be provided for achieving a desired plurality of distinct orientation angles.

An exemplary method for using the collection of trial shells 400a-440c will now be described. After the acetabular prosthesis 10 has been affixed to the patient, a first trial shell 400a may be positioned in the acetabular cup 12 by placing the trial screw 212 through the attachment passage 404a. The trial screw 212 is subsequently tightened to engage the threads 30 of the throughbore 28 in the locating position. If desired, the physician may rotate the trial shell 400a three-hundred-and-sixty (360) degrees about the orientation axis O to a predetermined location. The trial screw 212 is then tightened into the fastened position.

After this occurs, the physician determines if the proper angle is presented between the acetabular cup rim 240 and the trial cup rim 403a. This is accomplished by placing the head 308 of the femur 310 into the interior recess 402. The femur 310 is then moved through an appropriate range of motion to determine if the stem or neck 312 of the femur 310 engages any portion of the trial shell 400a. Additionally, it is determined if the head 308 dislocates from the trial shell 400a. If it is determined that the neck 312 of the femur 310 is contacting the trial shell 400a or the head 308 is dislocates from the trial shell 400a, the trial screw 212 is removed and the trial shell 400a is replaced by another trial shell 400b, 400c. The process is repeated until a selected trial shell 400 provides a favorable orientation angle that eliminates contact of any portion of the trial shell 400 with the neck 312 of a rotating femur 310 and precludes the head 308 from dislocating from the trial shell 400.

Finally, demarcations are noted on the trial shell 400 as described with respect to the trial cup 200. The demarcations are similarly included on the exterior or the prosthetic shell 320 and are used to match the orientation of the prosthetic shell 320 to the selected orientation. Thereafter, the femur 310 is dislocated from the inner recess 402 and the trial shell 400 is removed from the acetabular prosthesis 10. The prosthetic shell 320 is then placed into the acetabular prosthesis 10 according to the determined orientation of the trial shell 400.

Figure 26:
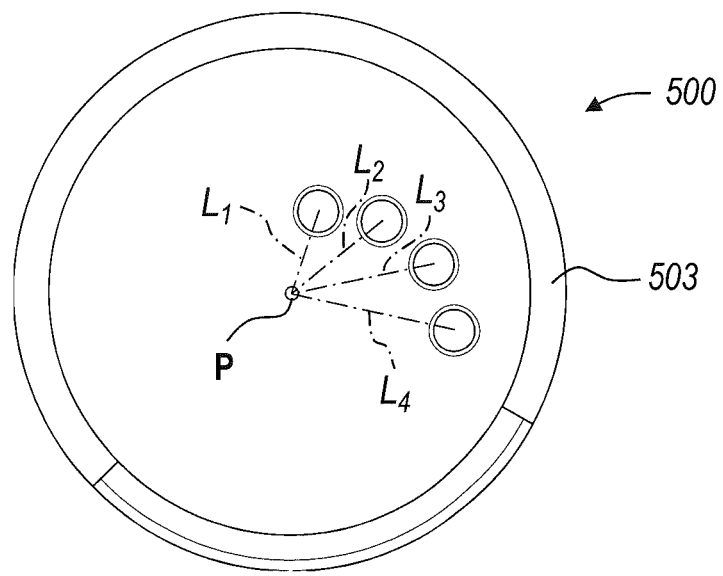
FIG. 26 is an elevated view of a trial cup according to a third embodiment.
Figure 27:
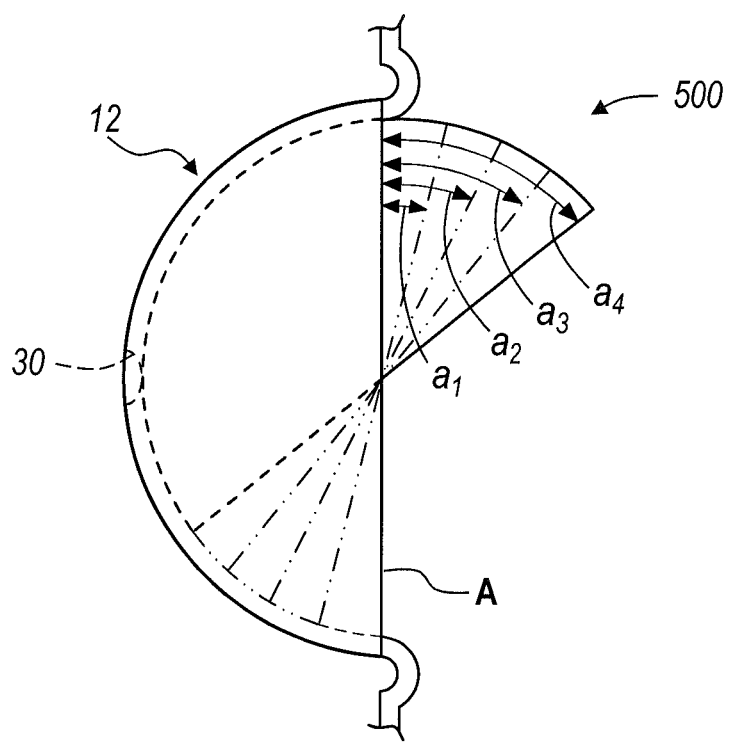
FIG. 27 is a side view of the trial cup of FIG. 26 illustrating a range of available orientation angles.

With reference to FIGS. 26 and 27, a trial shell 500 according to an alternate embodiment is shown having a plurality of passages 504a-504d incorporated thereon. The trial shell 500 provides a single shell having a plurality of mounting points yielding a plurality of angles ($a_1$-$a_4$) with respect to the plane A of the acetabular cup 12. Each passage 504a-504d is located a circumferential distance ($L_1$-$L_4$) from a point P intersecting the centerpoint of the radius defined by wall 503 of the trial shell 500. Again, while in the locating position, the acetabular cup 500 is moveable in one degree of freedom about the trial screw 212 in each passage 504a-504d. The angles $a_1$-$a_4$ preferably range from 0 to 40 degrees, however, alternate angles may similarly be provided.

Figure 28:
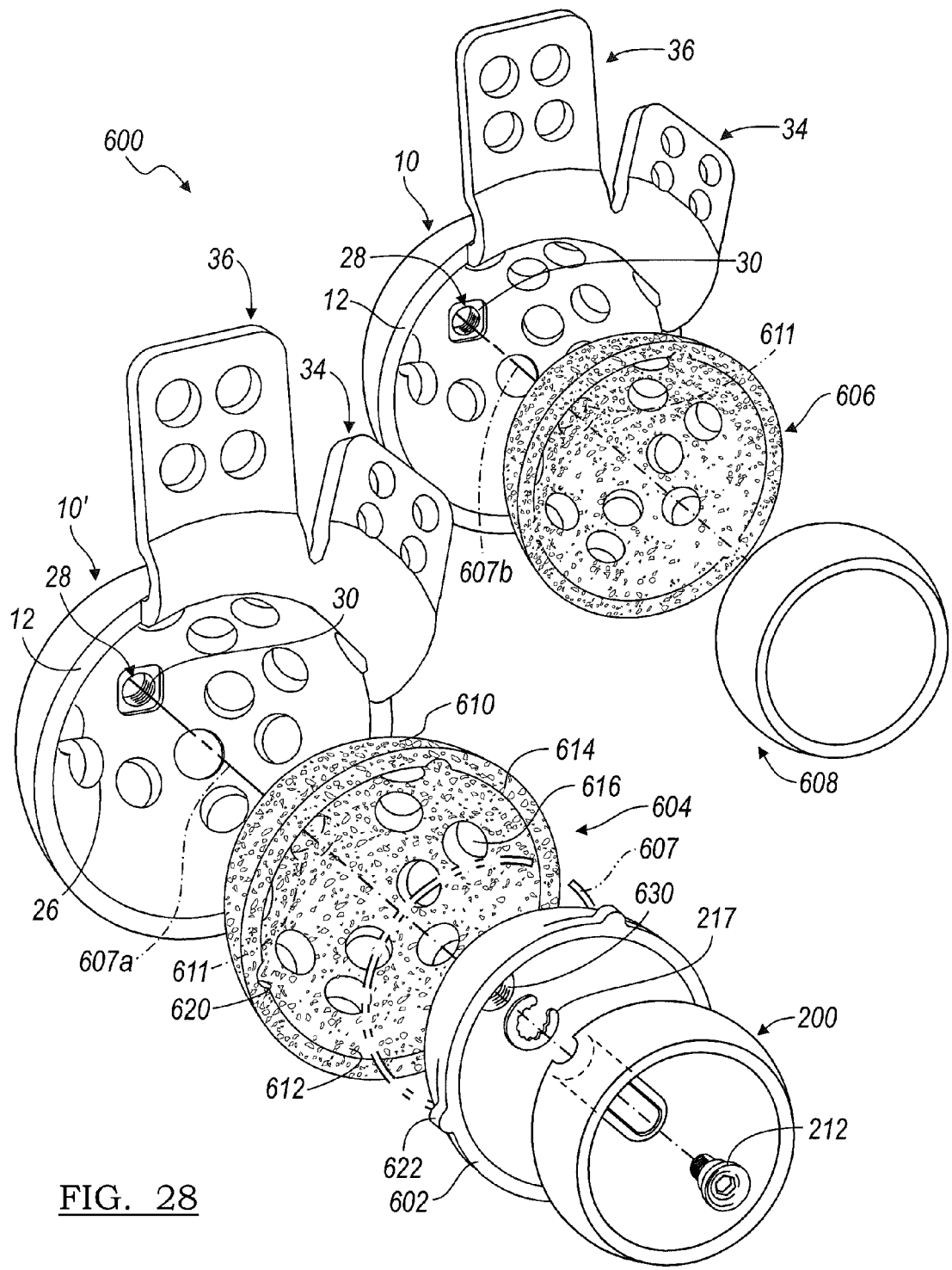
FIG. 28 is a kit view of a trialing system according to various embodiments.

A trialing system, according to various embodiments, can include an implant system 600, as illustrated in FIG. 28. The implant system 600 can include both trialing and permanently implantable portions, as discussed further herein. It will be understood, however, that additional or different implant and trial portions can be provided and those described herein are merely exemplary of the various portions that can be included in a system, such as the system 600.

Various trialing portions, such as a trial liner assembly that can include a trial cement mantle replicator 602, the trial bearing liner 200, the trial screw 212, and the trial protrusio cage 10', and a trial acetabular cup 604. The system 600 can also include implantable or permanent portions, such as an implantable or permanent acetabular cup 606, the implantable protrusio cage 10, and the implantable or permanent bearing liner 608. Therefore, one skilled in the art will understand that the system 600 can include both trialing portions and implantable or permanent portions. Further, it will be understood that the system 600 can be used in any appropriate manner so that a trial procedure need not only use trial portions, but may use a combination of permanent and trial portions. For example, the acetabular cup 604, 606 can be used or implanted without the protrusio cage 10, 10'. As illustrated and described herein, the acetabular cup 604, 606 can be implanted directly into a bone and the trial mantle 602 and the trial liner 200 can be positioned relative to the acetabular cup 604, 606 alone. The trial cement mantle 602 can be used to replicate a cement mantle that is formed during a procedure to hold or fix the cup 604 in place.

It will be understood that the trial liner 200, the protrusio cage 10, and the trial protrusio cage 10' can be substantially similar to those described above, and they are described in detail further herein. Nevertheless, it will be understood that the trial and permanent portions can be used in a procedure as described further herein.

The implantable acetabular cup 606, however, can include various portions such that the permanent liner 608 can be cemented into the interior of the permanent cup 606. The permanent cup 606 can substantially define a cup shape, and can include a substantially convex exterior 610 and concave interior 612. A rim 614 can define a thickness between the exterior wall 610 and the interior 612. It will be understood that the permanent cup 606, and even the trial cup 604, can include other portions, such as bores or screw holes 616, defined between the interior 612 and the exterior 610. Optionally, an apical hole or passage 611 can also be provided. The permanent cup 606 can be formed of a material that is substantially porous throughout. It will be understood, according to various embodiments, that the cup 606 need not be made of a completely porous material, but a completely porous material can include certain properties. A cup formed of a substantially or completely porous material, is described in currently pending U.S. patent application Ser. No. 11/357,868, entitled "Method And Apparatus For Use Of Porous Implants" and in currently pending U.S. patent application Ser. No. 11/546,500, entitled "Method And Apparatus For Use Of Porous Implants", both of these are incorporated herein by reference. The substantially porous material, which can include a porous material only positioned on the interior 612 of the permanent cup 606, can allow an adhering or cementing of the permanent liner 608 relative to the permanent cup 606. Various materials, such as bone cement, can be used to form a cement mantle to fix or hold the permanent liner 608 relative to the permanent cup 606.

As discussed above, the permanent cup 606 can be positioned in a prepared acetabulum, according to various embodiments. The permanent cup 606 can be positioned directly into a prepared acetabulum or positioned relative to a second implant, such as the protrusio cage 10. It may be selected, however, to trial the acetabular cup 606 and the various other portions, such as the liner, prior to permanently positioning the various portions relative to the anatomy. Therefore, the trial mantle 602 can be positioned relative to either the permanent cup 606 or the trial cup 604. It will be understood that either of the cups 604, 606 can be used, according to various embodiments. Both of the cups 604, 606 can include a receiving portion 620 to cooperate with an engaging portion 622 of the trial cement mantle 602. The receiving portion 620 can include a divot or depression that can receive the engaging portion 622, which can include a projection or finger. It will be understood that any appropriate engagement portion or cooperation portion can be provided, and the engagement finger 622, which can cooperate with the depression 620, is merely exemplary.

The trial mantle 602 can include any appropriate number of the projections 622, and three projections are illustrated merely for exemplary purposes, more can be included, as shown in phantom. Further, the cups 604, 606 can include any appropriate number of the cooperating portion 620 and three are provided merely for exemplary purposes. For example, the acetabular cups 604, 606 can include more of the receiving portion 620 than the trial cement mantle 602 includes the engaging member 622 to allow for a variety or multitude of possible positions of the trial mantle 602 relative to the cup 604, 606.

Figure 29:
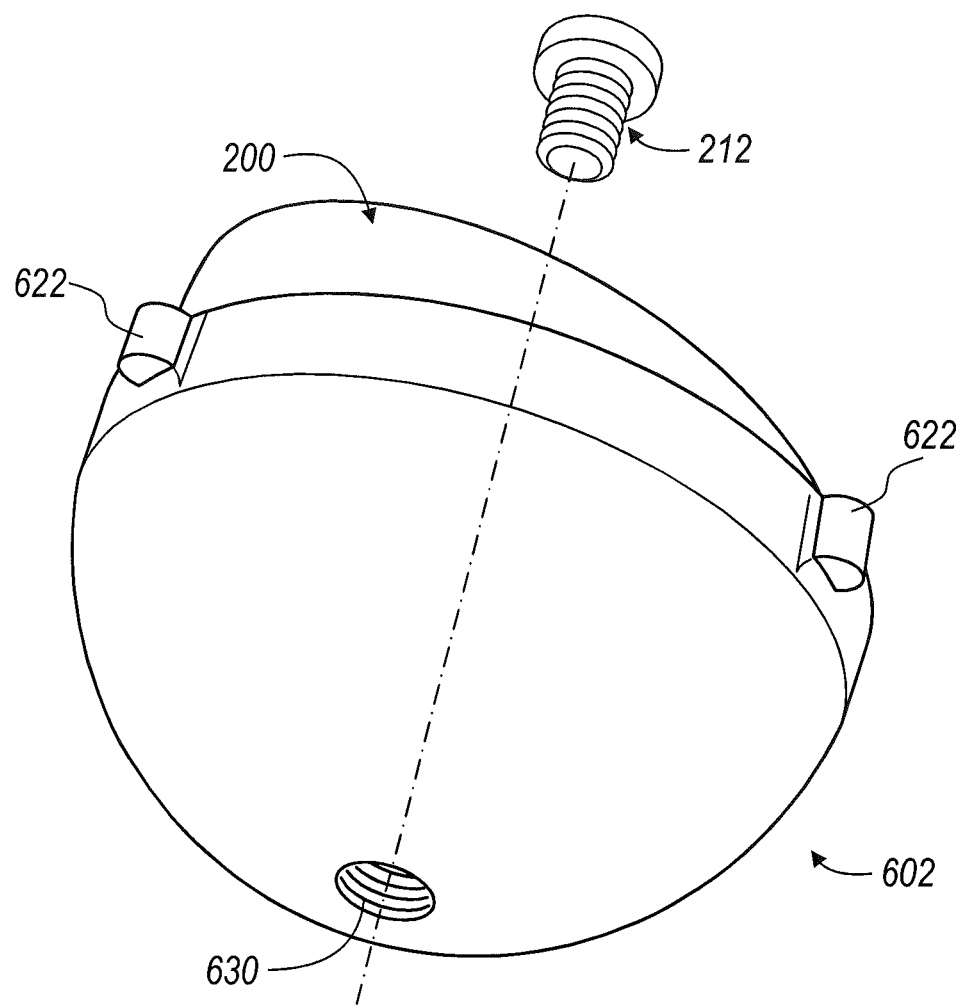
FIG. 29 is a bottom perspective view of a trial cement mantle and liner system, according to various embodiments.

The trial mantle 602 can include portions that cooperate with the trial liner 200 in a manner substantially similar to those of the protrusio cage 10. For example, the trial mantle 606 can include a positioning bore or engaging hole 630 that can be threaded and can cooperate with a trial screw or receive a portion of the trial screw 212. As illustrated in FIG. 29, the receiving bore 630 can be positioned near an apex or pole region of the trial cement mantle 602. It will be understood, however, that the engaging hole 630 can be positioned in any appropriate location through the trial cement mantle 602. The trial cement mantle 602 can then be positioned relative to the cup 604, 606 in any appropriate manner. The use of the screw 212 is merely exemplary and other connection mechanisms can be used. Optionally, the screw 212, or appropriate holding or locking portion, can engage or pass through the optional apical hole 611 in the cup 604, 606 and the apical hole 28 of the protrusio cage 10, 10'.

As discussed above, the trial liner 200 is fixed relative to a selected portion, such as the protrusio cage 10 or the trial cement mantle 602. The trial liner 200 is fixed in a selected position prior to trialing and allows a second portion of the anatomy, such as a femoral head or proximal femoral prosthesis, to be trialed relative to the trial bearing liner 200. It will be understood that the trialing can also occur with a second trial prosthesis. Nevertheless, the trial liner 200 is fixed in one of a plurality of orientations prior to contact or interaction with the second portion. The fixation can occur with the trial screw 212 positioned through the slot 204 of the trial liner 200.

As noted above, the trial liner 200 is fixed to all movement relative to the anatomy, trial mantle, etc. As discussed above, the screw 212 can be used to hold or compress each of the components together and fix them in a selected orientation. Also, the locking system, such as the locking washer 217, can hold the screw 212 relative to the trial line 200 prior to fixing or positioning the trial liner 200. This can assist a user in positioning the trial liner relative to the trial mantle 606. The trial system or implantable portions can be assembled as illustrated in FIG. 28 or include any selected portions thereof. Moreover, the axes 607a, 607b are exemplary of assembly axes if it is selected to position the cup 604, 606 within the protrusio cage 10, 10'.

As illustrated and discussed above, the various portions can be positioned relative to the pelvis 300 in the prepared acetabulum 302. One skilled in the art will understand, the implantable cup 606 can be similarly positioned within a prepared pelvis 300 alone and a detailed illustration and discussion is not therefore necessary. The use of the trial cement portion 602, however, is illustrated in FIGS. 30A and 30B.

Figure 30A:
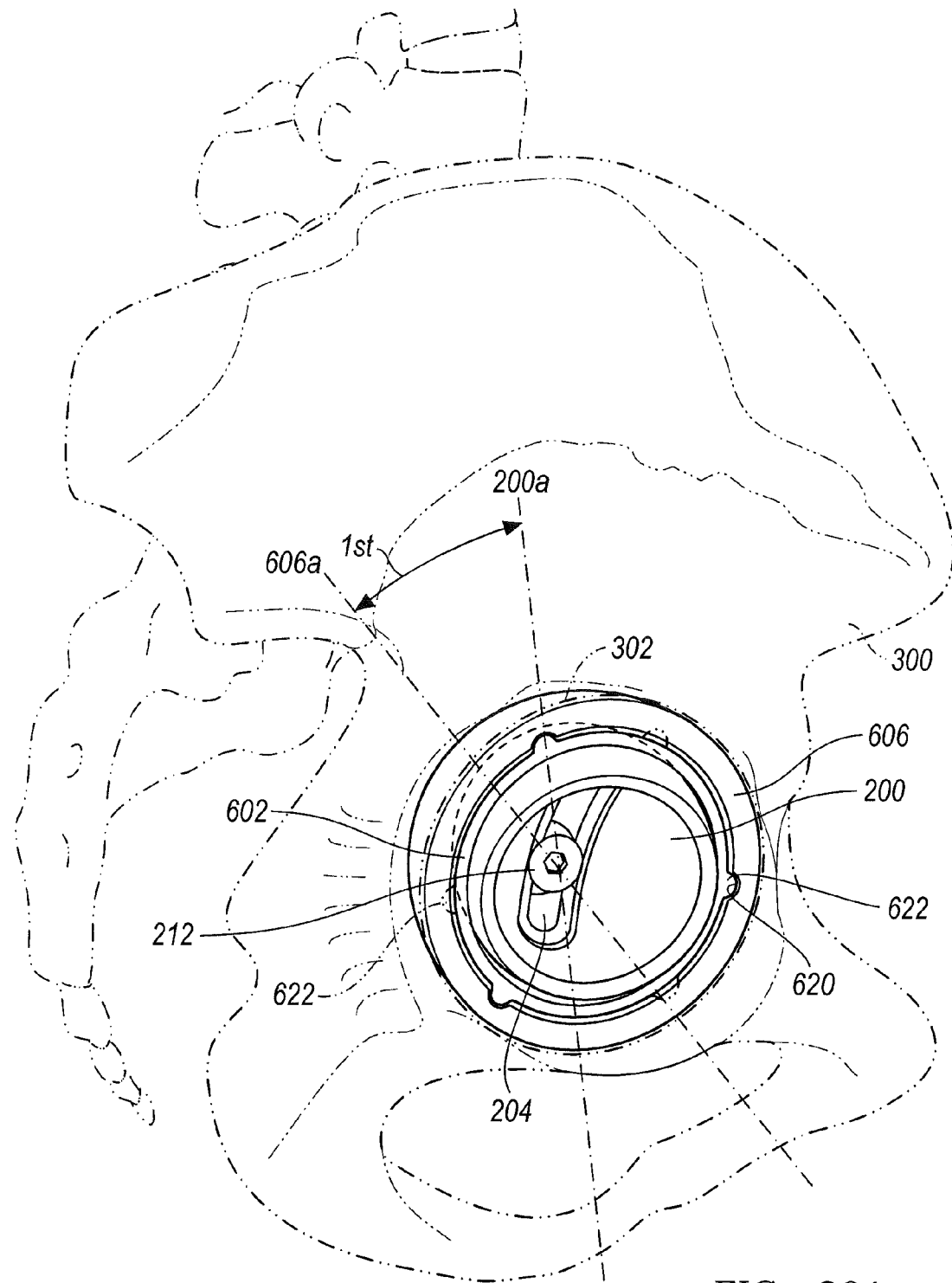
FIGS. 30A and 30B are environmental views of a trial system, according to various embodiments, in two different positions.
Figure 30B:
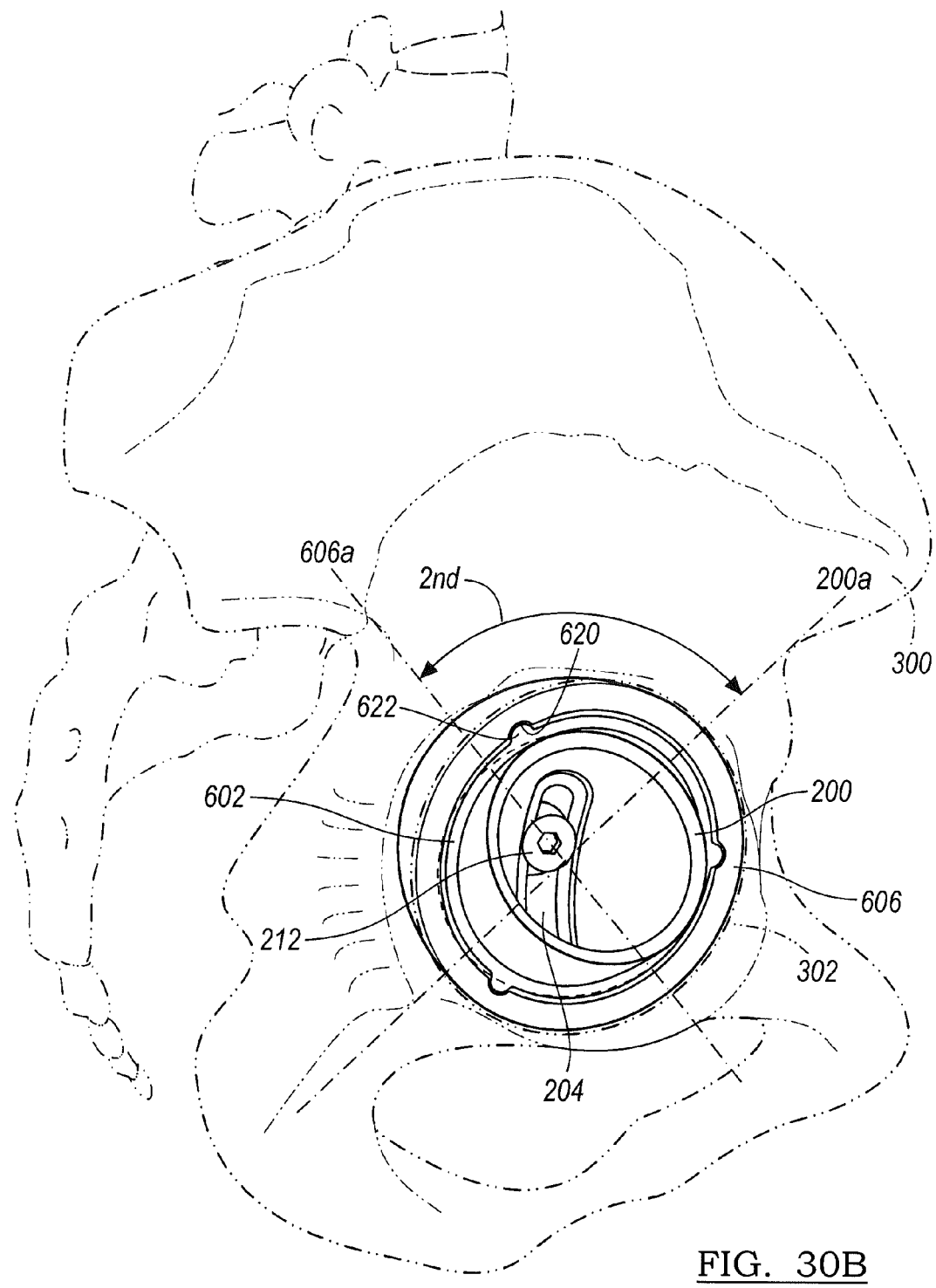

According to various embodiments, and with initial reference to FIG. 30A, the permanent cup 606 can be positioned in any appropriate location, such as the prepared acetabulum 302, illustrated above. As discussed above, it will be understood by one skilled in the art, the trial cup 604 may also be used to trial the trial liner 200, and the permanent cup 606 is illustrated herein merely for exemplary purposes. Further, the protrusio cage 10 or trial protrusio cage 10' can also be used with the acetabular cup 606. It will also be understood that the permanent cup 606 can be positioned relative to any appropriate portion of the anatomy and in any appropriate manner, such as with fixation screws, bone cement, a biologically acceptable cement, or any other appropriate manner. The permanent acetabular cup 606 can be substantially permanently fixed relative to the anatomy prior to the trialing of the trial liner 200. One skilled in the art will understand, however, that the acetabular cup 606 need not be permanently fixed prior to the trialing of the trial liner 200.

The discussion herein assumes the acetabular cup 606 is fixed relative to the anatomy. The trial cement mantle 602 can then be positioned relative to the cup 606. The trial cement mantle 602 can be positioned relative to the cup 606 in any appropriate manner. For example, the trial cement mantle 602 can include a friction fit or engagement within the interior 612 of the cup 606. Alternatively, or in addition thereto, the engagement portions 622 of the trial cement mantle 602 can positively engage the receiving portion 620 of the cup 606 to hold or assist in holding the trial cement mantle 602 relative to the cup 606. An additional example can include a snap ring that selectively interconnects the cup 606 and trial cement mantle 602. Other fastening or engagement portions can be provided, as known to one skilled in the art. Further, the trial screw 212, or any appropriate screw, can be used to assist in fixing the trial cement mantle 602 relative to the cup 606.

Either prior to, concurrently with, or after positioning the trial cement mantle 602 relative to the cup 606, the trial liner 200 is positioned and fixed relative to the trial cement mantle 602. As discussed above, the trial liner 200 can be positioned relative to the trial cement mantle 602 in any appropriate position or manner. For example, the trial screw 212 can be inserted and tightened through the slot 204 into the trial bore 630 of the trial cement mantle 602. In this manner, the trial liner 200 can be substantially fixed in a first selected position, such as that illustrated in FIG. 30A, for trialing the second portion or prosthesis (e.g. femoral head) relative to the fixed trial liner 200.

As illustrated in FIG. 30A, the trial liner 200 can include a central axis 200a that can be positioned at a first orientation relative to an axis 606a of the cup 606. The cup axis 606a can generally be defined as a longitudinal or central axis of an apical hole 611 of the cup 606. As illustrated in FIG. 28, an assembly axis 607a can be similar to the axis 606a defined by the cup 606. The axis of the cup 606a can generally be positioned at an angle relative to an anatomy of the patient. Generally the axis 606a passing through the apical hole 611 extends from the acetabulum and intersects a region of the anatomy superior to the acetabulum. Therefore, the axis 606a is at least positioned at an angle relative to the anatomy of the patient into which it is positioned and is not orthogonal or parallel to the sagittal plane of a patient. Moreover, the trial liner 200 is positioned relative to the axis 606a. Although the trial liner 200 defines a central axis 200a, the central axis of the trial liner 200 is illustrated merely to show the movement of the trial liner 200 relative to the axis 606a of the cup 606. As discussed herein, as the trial liner 200 moves, it moves relative to the axis 606a defined by the cup 606, which is at an angle relative to a longitudinal axis or sagittal plane of the patient.

With reference to FIG. 30B, the trial liner can be repositioned to a second orientation relative to the cup 606, in a manner substantially similar to that described above. In a second orientation, the trial screw 212 is used to fix the trial liner 200 relative to the cup 606 and the trial cement mantle 602. In this way, the trial liner 200 can achieve a second orientation relative to the cup 606. It will be understood that the second position or orientation, of the trial liner 200 relative to the cup 606 and the trial cement mantle 602, can include any appropriate number of trial positions.

The trial liner 200 defines the axis 200a that is positioned at a second orientation relative to the axis 606a of the cup 606. As discussed above, the trial liner 200 is moved about the axis 606a of the cup 606. The axis 200a, defined by the trial liner 200, can be repositioned relative to the axis 606a of the cup 606 by moving the trial liner 200. The trial liner 200 is then fixed in the second position with the screw 212 and a second trialing procedure can occur. In this way, with the trial liner can occur in multiple positions.

Once the trial liner 200 is fixed relative to the trial cement mantle 602 with the trial screw 212, or any other appropriate mechanism, the second portion can be trialed relative to the trial liner 200. As discussed above, a prosthesis can be trialed relative to the trial liner 200, however, a substantially natural portion can also be trialed relative to the trial liner 200. Therefore, one skilled in the art will understand that any appropriate portion can be trialed relative to the trial liner 200 in any of its fixed selected positions or orientations.

Trialing the second portion in the multiple positions of the trial liner 200 allows for a determination of an optimized position of the implantable liner 608, or any appropriate liner. The trialing can allow a user, such as a surgeon, to determine whether a position of the liner, as set with the trial liner 200, will cause impinging during movement, dislocate the second portion, etc. If an unselected event occurs, such as impingement, then an optimized position may not have been found. One skilled in the art will understand, however, that the complete lack of impingement or other event may not be possible and an optimized position may provide minimal impingement or least likelihood of dislocation. Nevertheless, multiple positions can be trialed with the trial liner 200 to determine the optimized position of the liner 608 for implantation.

Once the trial liner 200 has been trialed in an appropriate number of orientations, the permanent bearing liner 608 can be cemented relative to the cup 606. Any appropriate cementing procedure can be used, but the orientation of the implantable or permanent bearing liner 608 relative to the cup 606 can be determined or based upon the trialed positions of the trial liner 200. Therefore, the trial liner 200 can assist a user in determining a position of the permanent liner 608 relative to the cup 606.

The description of the various embodiments is merely exemplary in nature and, thus, variations that do not depart from the gist of the various embodiments are intended to be within the scope of the present disclosure and appended claims. Such variations are not to be regarded as a departure from the spirit and scope of the present disclosure and appended claims.

What is claimed is:

1. An acetabular prosthesis system to replace at least a portion of an acetabulum of an anatomy, the system comprising:
    a trial cup configured to be removably positioned relative to a first portion of the anatomy;
    a trial cement mantle member configured to be removably positioned in a selected first position relative to the positioned trial cup;
    a trial liner configured to be removably positioned at variable positions relative to the trial cement mantle member, the trial liner having an exterior convex surface, an interior concave surface opposite the exterior convex surface, a bottom edge defining a planar surface, and an elongated slot extending from the exterior convex surface to the interior concave surface, wherein the planar surface extends along a first reference plane, and wherein the elongated slot extends along a second reference plane generally perpendicular to the first reference plane; and
    a trial liner fixation member configured to removably secure the trial liner to the trial cement mantle member at each of the variable positions, the trial liner fixation member having a first portion extendable through the elongated slot of the trial liner,
    wherein the trial cement mantle member is positionable between the trial liner and the trial cup to replicate a cement mantle portion positionable between an implantable cup and an implantable liner,
    wherein the trial liner is configured to be positioned at variable positions relative to the trial cement mantle member, and
    wherein the elongated slot facilitates a range of motion of the trial liner relative to the trial cement mantle member.

2. The system of claim 1, wherein:
    an implantable cup configured to be is implanted relative to the first portion of the anatomy after the positioned trial cement mantle member and the positioned trial cup are removed.

3. The system of claim 1, wherein the first portion of the trial liner fixation member is a shank, the trial liner fixation member having a head portion configured to bear against the trial liner to hold the trial liner at each of the variable positions.

4. An acetabular prosthesis system to replace at least a portion of an acetabulum of an anatomy, the system comprising:
    a trial cup configured to be removably positioned relative to a first portion of the anatomy;
    a trial liner configured to be removably positioned relative to the trial cup, the trial liner having an exterior convex surface, an interior concave surface opposite the exterior convex surface, a bottom edge defining a planar surface, a top-most portion defined at a position on the interior concave surface having a greatest distance from the planar surface, and an elongated slot extending from the exterior convex surface to the interior concave surface at the top-most
    a trial cement mantle member configured to be removably positioned between the positioned trial cup and the trial liner to replicate a cement mantle portion between an implantable cup and an implantable liner; and
    a holding member configured to be received through the elongated slot and hold the trial liner in a selected first position or a selected second position relative to the trial cement mantle member, the selected first position different than the selected second position,
    wherein the trial liner is configured to be positioned at variable positions relative to the trial cement mantle member, and
    wherein the elongated slot facilitates a range of motion of the trial liner relative to the trial cement mantle member.

5. The system of claim 4, further comprising:
    an implantable cup configured to be implanted in an acetabulum;
    an implantable liner configured to be cemented in the implanted implantable cup in a position substantially similar to the first position of the trial liner after removing the positioned trial cement mantle and the positioned trial cup.

6. The system of claim 4, wherein the trial cement mantle member includes a cooperation system including a indent on the trial cup and a projection on the trial cement mantle member;
    wherein the projection is configured to engage the indent.

7. The system of claim 4, further comprising:
    a protrusio cage positionable relative to the first portion of the anatomy;
    wherein the trial cup is configured to be positioned in the protrusio cage.

8. An acetabular prosthesis trialing system, the system comprising:
    a trial cup configured to be removably implantable in an acetabulum of a patient;
    a trial cement mantle member configured to be removably positioned relative to the implanted trial cup; and a trial liner configured to be removably positioned at a plurality of positions relative to the trial cement mantle member, the trial liner having an exterior convex surface, an interior concave surface opposite the exterior convex surface, and an elongated slot extending from the exterior convex surface to the interior concave surface; and a trial screw configured to be received through the elongated slot of the trial liner and fix the trial liner in a selected position relative to the implanted trial cup, wherein the trial cement mantle member is positionable between the trial liner and the trial cup to replicate a cement mantle portion positionable between an implantable cup and an implantable liner, and wherein the elongated slot defines an arc of at least 60 degrees to facilitate a range of motion of the trial liner relative to the trial cement mantle member.

9. The system of claim 8, wherein the arc of the elongated slot is between about 60 degrees and about 120 degrees.

* * * * *